United States Patent [19]

Gleason et al.

[11] Patent Number: 4,820,719

[45] Date of Patent: Apr. 11, 1989

[54] LEUKOTRIENE ANTAGONISTS

[75] Inventors: John G. Gleason, Downingtown; Ralph F. Hall, Villanova; Thomas Wen-Fu Ku, Dresher; Carl D. Perchonock, Philadelphia, all of Pa.

[73] Assignee: SmithKline Beckman Corporation, Philadelphia, Pa.

[21] Appl. No.: 195,355

[22] Filed: May 16, 1988

Related U.S. Application Data

[63] Continuation of Ser. No. 926,314, Oct. 31, 1986, abandoned, which is a continuation-in-part of Ser. No. 848,608, Apr. 7, 1986, abandoned, which is a continuation-in-part of Ser. No. 725,264, Apr. 19, 1985, abandoned.

[51] Int. Cl.$^4$ ................. A61K 31/41; C07D 233/64
[52] U.S. Cl. ........................ 514/381; 514/398; 514/561; 514/570; 514/616; 514/618; 548/242; 548/253; 548/337; 562/426; 562/429; 562/430; 558/396; 564/154; 564/162
[58] Field of Search ............ 548/252, 253, 337; 514/381, 398, 562, 570, 616, 618; 562/426, 429, 430; 564/154, 162; 558/396

[56] References Cited

U.S. PATENT DOCUMENTS 4,069,744  9/1986  Young et al. ............... 549/402

FOREIGN PATENT DOCUMENTS

| 68739 | 1/1983 | European Pat. Off. |
| 123543 | 10/1984 | European Pat. Off. ........... 549/402 |
| 132367 | 1/1985 | European Pat. Off. ........... 548/132 |
| 2746754 | 4/1978 | Fed. Rep. of Germany. |
| 1397647 | 6/1975 | United Kingdom ............ 562/426 |
| 2144422A | 3/1985 | United Kingdom ............ 548/252 |

OTHER PUBLICATIONS

Chemical Abstracts, vol. 96, 98909h (1982).

*Primary Examiner*—Mary C. Lee
*Assistant Examiner*—Mary Sue Howard
*Attorney, Agent, or Firm*—Nancy S. Mayer; Janice E. Williams; Alan D. Lourie

[57] ABSTRACT

This invention relates to alkanoic acid compounds having phenyl and thio substituents which are useful as leukotriene antagonists and pharmaceutical compositions containing such compounds. This invention also relates to methods of treating diseases in which leukotrienes are a factor by administration of an effective amount of the above compounds or compositions.

39 Claims, No Drawings

LEUKOTRIENE ANTAGONISTS

This is a continuation of application Ser. No. 926,314, filed Oct. 31, 1986, now abandoned, which is a continuation-in-part application of Ser. No. 848,608 filed Apr. 7, 1986 now abandoned which is a continuation-in-part application of Ser. No. 725,264 filed Apr. 19, 1985 now abandoned.

BACKGROUND OF THE INVENTION

"Slow Reacting Substance of Anaphylaxis" (SRS-A) has been shown to be a highly potent bronchoconstricting substance which is released primarily from mast cells and basophils on antigenic challenge. SRS-A has been proposed as a primary mediator human asthma. SRS-A, in addition to its pronounced effects on lung tissue, also produces permeability changes in skin and may be involved in acute cutaneous allergic reactions. Further, SRS-A has been shown to effect depression of ventricular contraction and potentiation of the cardiovascular effects of histamine.

The discovery of the naturally occurring leukotrienes and their relationship to SRS-A has reinforced interest in SRS-A and other arachidonate metabolites. SRS-A derived from mouse, rat, guinea pig and man have all been characterized as mixtures of leukotriene-$C_4$ ($LTC_4$), leukotriene-$D_4$ ($LTD_4$) and leukotriene-$E_4$ ($LTE_4$), the structural formulae of which are represented below.

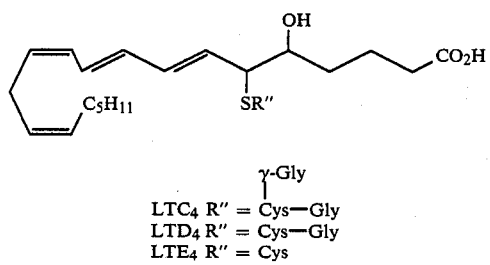

$LTC_4$ R'' = Cys—Gly (γ-Gly)
$LTD_4$ R'' = Cys—Gly
$LTE_4$ R'' = Cys

Leukotrienes are a group of eicosanoids formed from arachidonic acid metabolism via the lipoxygenase pathway. These lipid derivatives originate from $LTA_4$ and are of two types: (1) those containing a sulfidopeptide side chain ($LTC_4$, $LTD_4$, and $LTE_4$), and (2) those that are nonpeptidic ($LTB_4$). Leukotrienes comprise a group of naturally occurring substances that have the potential to contribute significantly to the pathogenesis of a variety of inflammatory and ischemic disorders. The pathophysiological role of leukotrienes has been the focus of recent intensive studies.

As summarized by Lefer, A. M., *Biochemical Pharmacology*, 35, 2, 123–127 (1986) both the peptide and non-peptide leukotrienes exert microcirculatory actions, promoting leakage of fluid across the capillary endothelial membrane in most types of vascular beds. $LTB_4$ has potent chemotactic actions and contributes to the recruitment and adherence of mobile scavenger cells to the endothelial membrane. $LTC_4$, $LTD_4$ and $LTE_4$ stimulate a variety of types of muscles. $LTC_4$ and $LTD_4$ are potent bronchoconstrictors and effective stimulators of vascular smooth muscle. This vasoconstrictor effect has been shown to occur in pulmonary, coronary, cerebral, renal, and mesenteric vasculatures.

Leukotrienes have been implicated in a number of pulmonary diseases. Leukotrienes are known to be potent bronchoconstrictors in humans. LTC and LTD have been shown to be potent and selective peripheral airway agonists, being more active than histamine. (See Drazen, J. M. et al., *Proc. Nat'l. Acad. Sci. USA*, 77, 7, 4354–4358 (1980)). $LTC_4$ and $LTD_4$ have been shown to increase the release of mucus from human airways in vitro. (See Matrom, Z. et al., *Am. Rev. Respir. Dis.*, 126, 449–451 (1982).) The leukotriene antagonists of the present invention can be useful in the treatment of allergic or non-allergic bronchial asthma or pulmonary anaphylaxis.

The presence of leukotrienes in the sputum of patients having cystic fibrosis chronic bronchitis, and bronchiectasis at levels likely to have pathophysiological effects has been demonstrated by Zakrzewski, et al. (See Zakrzewski, J. T. et al., *Prostaglandins*, 28, 5, 641 (1984).) Treatment of these diseases constitutes additional possible utility for leukotriene antagonists.

Leukotrienes have been identified in the nasal secretions of allergic subjects who underwent in vivo challenge with specific antigen. The release of the leukotrienes was correlated with typical allergic signs and symptoms. (See Creticos, P. S. et al., *New England J. of Med.*, 310, 25, 1626–1629 (1984).) This suggests that allergic rhinitis is another area of utility for leukotriene antagonists.

The role of leukotrienes and the specificity and selectivity of a particular leukotriene antagonist in an animal model of the adult respiratory distress syndrome was investigated by Snapper et al. (See Snapper, J. R. et al., *Abstracts of Int'l Conf. on Prostaglandins and Related Comp.*, Florence, Italy, p. 495 (June 1986).) Elevated concentrations of $LTD_4$ were shown in pulmonary edema fluid of patients with adult respiratory distress syndrome. (See Matthay, M. et al., *J. Clin. Immunol.*, 4, 479–483 (1984).) Markedly elevated leukotriene levels have been shown in the edema fluid of a patient with pulmonary edema after cardiopulmonary bypass. (See Swerdlow, B. N., et al., *Anesth. Analg.*, 65, 306–308, (1986).) $LTC_1$ and LTD have also been shown to have a direct systemic arterial hypotensive effect and produce vasoconstriction and increased vasopermeability. (See Drazen et al., ibid.) This suggests leukotriene antagonists can also be useful in the areas of adult respiratory distress syndrome, pulmonary edema, and hypertension.

Leukotrienes have also been directly or indirectly implicated in a variety of non-pulmonary diseases in the ocular, dermatologic, cardiovascular, renal, trauma, inflammatory, carcinogenic and other areas.

Further evidence of leukotrienes as mediators of allergic reactions is provided by the identification of leukotrienes in tear fluids from subjects following a conjunctival provocation tests and in skin blister fluids after allergen challenge in allergic skin diseases and conjunctival mucosa. (See Bisgaard, H., et al., *Allergy*, 40, 417–423 (1985).) Leukotriene immunoreactivity has also been shown to be present in the aqueous humor of human patients with and without uveitis. The concentrations of leukotrienes were sufficiently high that these mediators were expected to contribute in a meaningful way to tissue responses. (See Parker, J. A. et al., Arch Ophthalmol, 104, 722–724 (1986).) It has also been demonstrated that psoriatic skin has elevated levels of leukotrienes. (See Ford-Hutchinson, *J. Allergy Clin. Immunol.*, 74, 437–440 (1984).). Local effects of intracutaneous injections of synthetic leukotrienes in human skin were demonstrated by Soter et al. (See Soter et al., *J. Clin Invest Dermatol*, 80, 115–119 (1983).) Cutaneous vasodilation with edema formation and a neutrophil infiltrate were induced. Leukotriene synthesis inhibitors or leukotriene antagonists can also be useful in the treatment of ocular or dermatological diseases such as allergic conjunctivitis, uveltis, allergic dermatitis or psoriasis.

Another area of utility for leukotriene antagonists is in the treatment of cardiovascular diseases. Since peptide leukotrienes are potent coronary vasoconstrictors, they are implicated in a variety of cardiac disorders including arrhythmias, conduction blocks and cardiac depression. Synthetic leukotrienes have been shown to be powerful myocardial depressants, their effects consisting of a decrease in contractile force and coronary flow. The cardiac effects of $LTC_4$ and $LTD_4$ have been shown to be antagonized by a specific leukotriene antagonist, thus suggesting usefulness of leukotriene antagonists in the areas of myocardial depression and cardiac anaphylaxis. (See Burke, J. A., et al., *J. Pharmacology and Experimental Therapeutics*, 221, 1, 235–241 (1982).)

$LTC_4$ and $LTD_4$ have been measured in the body fluids of rats in endotoxic shock, but are rapidly cleared from the blood into the bile. Thus leukotrienes are formed in ischemia and shock. Specific inhibitors of leukotriene biosynthesis reduce the level of leukotrienes and therefore reduce manifestations of traumatic shock, endotoxic shock, and acute myocardial ischemia. Leukotriene receptor antagonists have also been shown to reduce manifestations of endotoxic shock and to reduce extension of infarct size. Administration of peptide leukotrienes has been shown to produce significant ischemia or shock. (See Lefer, A. M., *Biochemical Pharmacology*, 35, 2, 123–127 (1986).) Thus further areas of utility for leukotriene antagonists can be the treatment of myocardial ischemia, acute myocardial infarction, salvage of ischemic myocardium, angina, cardiac arrhythmias, shock and atherosclerosis.

Leukotriene antagonists can also be useful in the area of renal ischemia or renal failure. Badr et al. have shown that $LTC_4$ produces significant elevation of mean arterial pressure and reductions in cardiac output and renal blood flow, and that such effects can be abolished by a specific leukotriene antagonist. (See Badr, K. F. et al., *Circulation Research*, 54, 5, 492–499 (1984).) Leukotrienes have also been shown to have a role in endotoxin-induced renal failure and the effects of the leukotrienes selectively antagonized in this model of renal injury. (See Badr, K. F., et al., *Kidney International*, 30, 474–480 (1986). $LTD_4$ has been shown to produce local glomerular constrictor actions which are prevented by treatment with a leukotriene antagonist. (See Badr, K. F. et al., *Kidney International*, 29, 1, 328 (1986).) $LTC_4$ has been demonstrated to contact rat glomerular mesangial cells in culture and thereby effect intraglomerular actions to reduce filtration surface area. (See Dunn, M. J. et al., *Kidney International*, 27, 1, 256 (1985).) Thus another area of utility for leukotriene antagonists can be in the treatment of glomerulonephritis.

Leukotrienes have also been indicated in the area of transplant rejection. An increase in cardiac and renal allograft survival in the presence of a leukotriene receptor antagonist was documented by Foegh et al. (See Foegh, M. L. et al. *Advances in Prostaglandin, Thromboxane, and Leukotriene Research*, 13, 209–217 (1985).) Rejection of rat renal allografts was shown to produce increased amounts of $LTC_4$. (See Coffman, T. M. et al., *Kidney International*, 29, 1, 332 (1986).)

A further area of utility for leukotriene antagonists can be in treatment of tissue trama, burns, or fractures. A significant increase in the production of cysteinyl leukotrienes was shown after mechanical or thermal trauma sufficient to induce tissue edema and circulatory and respiratory dysfunction. (See Denzlinger, C. et al., *Science*, 230, 330–332 (1985).)

Leukotrienes have also been shown to have a role in acute inflammatory actions. $LTC_4$ and $LTD_4$ have potent effects on vascular caliber and permeability and $LTB_4$ increases leukocyte adhesion to the endothelium. The arteriolar constriction, plasma leakage, and leukocyte adhesion bear close resemblance to the early events in acute inflammatory reactions. (See Dahlen, S. E. et al., *Proc. Natl. Acad. Sci. USA*, 78, 6, 3887–3891 (1981).) Mediation of local homeostasis and inflammation by leukotrienes and other mast cell-dependent compounds was also investigated by Lewis et al. (See Lewis, R. A. et al., *Nature*, 293, 103–108 (1981).) Leukotriene antagonists can therefore be useful in the treatment of inflammatory diseases including rheumatoid arthritis and gout.

Cysteinyl leukotrienes have also been shown to undergo enterohepatic circulation, and thus are indicated in the area of inflammatory liver disease. (See Denzlinger, C. et al., *Prostaglandins Leukotrienes and Medicine*, 21, 321–322 (1986).) Leukotrienes can also be important mediators of inflammation in inflammatory bowel disease. (See Peskar, B. M. et al., *Agents and Actions*, 18, 381–383 (1986).) Leukotriene antagonists thus can be useful in the treatment of inflammatory liver and bowel disease.

Leukotrienes have been shown to modulate IL-1 production by human monocytes. (See Rola-Pleszczynski, M. et al., *J. of Immun.*, 135, 6, 3958–3961 (1985).) This suggests that leukotriene antagonists may play a role in IL-1 mediated functions of monocytes in inflammation and immune reactions.

$LTA_4$ has been shown to be a factor in inducing carcinogenic tumors and is considered a link between acute immunologic defense reactions and carcinogenesis. Leukotriene antagonists can therefore possibly have utility in treatment of some types of carcinogenic tumors. (See Wischnewsky, G. G. et al., *Anticancer Res.* 5, 6, 639 (1985).)

Leukotrienes have been implicated in gastric cytodestruction and gastric ulcers. Damage of gastro intestinal mucosa because of potent vasoconstriction and stasis of blood flow is correlated with increased levels of $LTC_4$. Functional antagonism of leukotriene effects may represent an alternative in treatment of mucosal injury. (See Dreyling, K. W. et al., *British J. Pharmacology*, 88, 236P (1986), and Peskar, B. M. et al. Prostaglandins, 31, 2, 283–293 (1986).) A leukotriene antagonist has been shown to protect against stress-induced gastric ulcers in rats. (See Ogle, C. W. et al., *IRCS Med. Sci.*, 14, 114–115 (1986).)

Other areas in which leukotriene antagonists can have utility because leukotrienes are indicated as mediators include prevention of premature labor (See Clayton, J. K. et al., *Proceedings of the BPS*, 573P, 17–19 Dec. 1984); treatment of migraine headaches (See Gazzaniga, P. P. et al., *Abstracts Int'l Conf. on Prostaglandins and Related Comp.*, 121, Florence, Italy (June 1986)); and treatment of gallstones (See Doty, J. E. et al., *Amer. J.* of *Surgery*, 145, 54–61 (1983) and Marom, Z. et al., *Amer. Rev. Respir. Dis.*, 126, 449–451 (1982).)

By antagonizing the effects of $LTC_4$, $LTD_4$ and $LTE_4$ or other pharmacologically active mediators at the end organ, for example airway smooth muscle, the compounds and pharmaceutical compositions of the instant invention are valuable in the treatment of diseases in subjects, including human or animals, in which leukotrienes are a key factor.

DETAILED DESCRIPTION OF THE INVENTION

The compounds of this invention are represented by the following general structural formula (I)

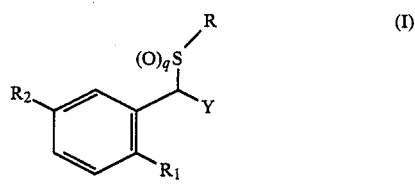

wherein $R_1$ is $C_8$ to $C_{13}$ alkyl, $C_7$ to $C_{12}$ alkoxy, $C_7$ to $C_{12}$ alkylthio, $C_{10}$ to $C_{12}$ 1-alkylnyl, 10-undecynyloxy, 11-dodecynyl, phenyl-$C_4$ to $C_{10}$ alkyl, phenyl-$C_3$ to $C_9$ alkoxy, phenylthio-$C_3$ to $C_9$ alkyl with the phenyl optionally mono substituted with bromo, chloro, trifluoromethyl, $C_1$ to $C_4$ alkoxy, methylthio or trifluoromethylthio, furyl-$C_4$ to $C_{10}$ alkyl, trifluoromethyl-$C_7$ to $C_{12}$ alkyl or cyclohexyl-$C_4$ to $C_{10}$ alkyl;

$R_2$ is hydrogen, bromo, chloro, methyl, trifluoromethyl, hydroxy, $C_1$ to $C_4$ alkoxy or nitro; or $R_1$ is hydrogen and $R_2$ is $C_8$ to $C_{13}$ alkyl, $C_7$ to $C_{12}$ alkoxy, $C_7$ to $C_{12}$ alkylthio, $C_{10}$ to $C_{12}$ 1-alkynyl, 10-undecynyloxy, 11-dodecynyl, phenyl-$C_4$ to $C_{10}$ alkyl, phenyl-$C_3$ to $C_9$ alkoxy, phenylthio-$C_3$ to $C_9$ alkyl with the phenyl optionally mono substituted with bromo, chloro, trifluoromethyl, $C_1$ to $C_4$ alkoxy, methylthio or trifuoromethylthio, furyl-$C_4$ to $C_{10}$ alkyl, trifluoromethyl-$C_7$ to $C_{12}$ alkyl or cyclohexyl-$C_4$ to $C_{10}$ alkyl;

q is 0, 1 or 2, with the proviso that any of $R_1$ and $R_2$ above are not alkylthio or phenylthioalkyl when q is 1 or 2;

Y is $COR_3$,

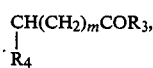

or $(CH_2)_{0-1}$-tetrazol-5-yl;

$R_3$ is hydroxy, amino, or $C_1$ to $C_6$ alkoxy;

$R_4$ is hydrogen, methyl, $C_1$ to $C_4$ alkoxy, fluoro or hydroxy;

m is 0, 1, and 2;

R is

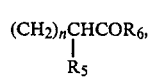

$CH(CO_2H)CH_2CO_2H$, $CH_2CH_2Z$ or

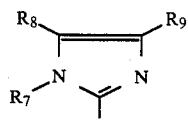

n is 0 to 6;

$R_5$ is hydrogen, amino, or $NHCOCH_2CH_2CH(NH_2)CO_2H$;

$R_6$ is hydroxy, amino, $NHCH_2CO_2H$, or $C_1$ to $C_6$ alkoxy;

Z is $SO_3H$, $SO_2NH_2$ or $CN$;

$R_7$ is hydrogen, $C_1$ to $C_4$ alkyl or $C_3$ to $C_4$ alkenyl;

$R_8$ is hydrogen, $C_1$ to $C_4$ alkyl, carboxyl or carboxamido, or $(CH_2)_pCO_2R_{12}$, wherein p is 1 or 2, $R_{12}$ is $C_1$ to $C_6$ alkyl, or hydrogen, when $R_7$ and $R_9$ are hydrogen or $C_1$ to $C_4$ alkyl; and $R_9$ is hydrogen, $C_1$ to $C_4$ alkyl or $CH_2CO_2R_{13}$ wherein $R_{13}$ is $C_1$ to $C_6$ alkyl, or hydrogen, with the proviso that when n is 0, $R_5$ is hydrogen and further that $R_7$, $R_8$ and $R_9$ are not all hydrogen; or a pharmaceutically acceptable salt thereof.

The term phenylthioalkyl is used to mean

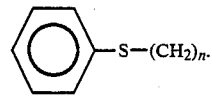

The ester and diester compounds of Formula (I) are subject to the further proviso that $R_3$ and $R_6$ are not both hydroxy or $R_3$ is not hydroxy if both $R_{12}$ and $R_{13}$ are hydrogen.

A particular class of compounds of this invention are the substituted alkanoic acid analogs of formula (I) represented by the structural formula (II)

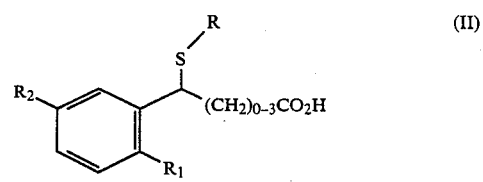

wherein $R_1$, $R_2$ and R are described above.

Particular members of this class of compounds are those represented by the structural formula (II) wherein R is $(CH_2)_{1-3}CO_2H$ or

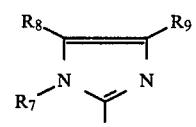

and $R_1$, $R_2$, $R_7$, $R_8$ and $R_9$ are described above.

A subgeneric class of these compounds are the diacid derivatives represented by the following general structural formula (III)

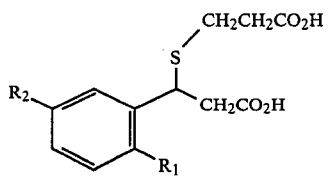 (III)

wherein $R_1$ and $R_2$ are described above, and particularly where $R_1$ is phenylalkyl.

The compounds of the formula (III) are exemplified by the following compounds:
(1) 3-(2-carboxyethylthio)-3-(2-dodecylphenyl)propanoic acid;
(2) 3-(2-carboxyethylthio)-3-[2-(8-phenyloctyl)phenyl]propanoic acid; and
(3) 3-(2-carboxyethylthio)-3-[2-(8-phenyloctyl)-5-trifluoromethylphenyl]propanoic acid.

A second subgeneric class of compounds of formula (II) are the diacid derivatives represented by the following structural formula (IV)

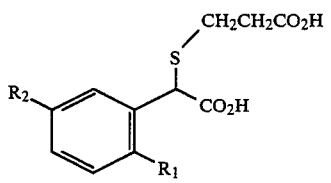 (IV)

wherein $R_1$ and $R_2$ are described above, and particularly where $R_1$ is phenylalkyl.

The compounds of the formula (IV) are exemplified by the following compounds:
(1) 2-(2-carboxyethylthio)-2-(2-dodecylphenyl)acetic acid; and
(2) 2-(2-carboxyethylthio)-2-[2-(8-phenyloctyl)phenyl]acetic acid.

A third subgeneric class of compounds of formula (II) are the heterocyclic derivatives represented by the following general structural formula (V)

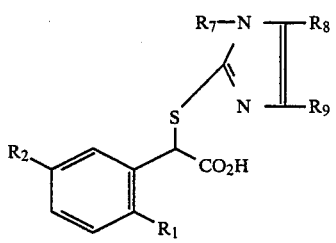 (V)

wherein $R_1$, $R_2$, $R_7$, $R_8$ and $R_9$ are described above.

The compounds of the formula (V) are exemplified by the following compounds:
(1) 2-(2-dodecylphenyl)-2-(1-methyl-4-propyl-5-carboxy-2-imidazolylthio]acetic acid; and
(2) 2-(2-dodecylphenyl)-2-(1,4-dimethyl-5-carboxy-2-imidazolylthio)acetic acid.

A further particular class of compounds of this invention are the hydroxy substituted alkanoic acid analogs of formula (I) represented by the structural formula (VI)

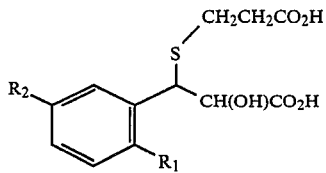 (VI)

wherein $R_1$ and $R_2$ are described above, and particularly where $R_1$ is phenylalkyl.

The compounds of the formula (VI) are exemplified by the following compounds:
(1) 3-(2-carboxyethylthio)-3-(2-dodecylphenyl)-2-hydroxypropanoic acid; and
(2) 3-(2-carboxyethylthio)-3-[2-(8-phenyloctyl)phenyl]-2-hydroxypropanoic acid.

A further class of compounds of this invention are the tetrazolyl substituted analogs of formula (I) represented by the structural formula (VII)

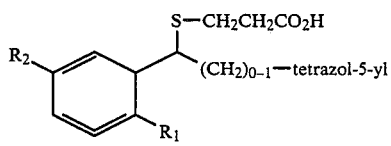 (VII)

wherein $R_1$ and $R_2$ are described above.

The compounds of the formula (VII) are exemplified by the following compounds:
(1) 4-thia-5-(2-dodecylphenyl)-5-(tetrazol-5-yl)pentanoic acid; and
(2) 4-thia-5-(2-dodecylphenyl)-6-(tetrazol-5-yl)hexanoic acid.

Some of the compounds of the formula (I) contain two asymmetric centers, such as when $R_4$ is methyl, methoxy, fluoro or hydroxy, or R is $CH(CO_2H)CH_2CO_2H$. This leads to the possibility of four stereoisomers for each such compound. In practice, these compounds are prepared as a mixture of two stereoisomers. Resolution procedures employing, for example, optically active amines furnish the separated enantiomers.

The compounds of the present invention, depending on their structure, are capable of forming salts with pharmaceutically acceptable acids and bases, according to procedures well known in the art. Such acceptable acids include inorganic and organic acids, such as hydrochloric, sulfuric, methanesulfonic, benzenesulfonic, p-toluenesulfonic and acetic acid. Such acceptable bases include organic and inorganic bases, such as ammonia, arginine, organic amines, alkali metal bases and alkaline earth metal bases. Of particular utility are the dipotassium, disodium, dimagnesium, and dicalcium salts of the diacid compounds of formula (I).

The compounds of the formula (I) wherein Y is $CO_2H$ are conveniently prepared from an aldehyde precursor of the following structural formula (VIII):

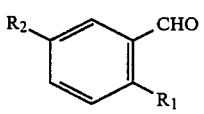 (VIII)

wherein $R_1$ and $R_2$ are described above. A compound of formula (VIII) is treated with trimethylsilyl cyanide in the presence of zinc iodide at low temperatures in an inert solvent to form the trimethylsilyl-protected cyanohydrin. Treatment of this with gaseous hydrogen chloride in methanol provides the methyl 2-hydroxyacetate derivative which is converted to the 2-chloroacetate with thionyl chloride. This valuable intermediate is then reacted with a substituted thiol selected to give, after removal of ester protective groups, a product of formula (I).

The compounds of the formula (I) wherein Y is $CH_2CO_2H$ are prepared by reacting the appropriate aldehyde of the formula (VIII) and an esterified bromoacetate, conveniently t-butyl bromoacetate, with a mixture of diethyl aluminum chloride, zinc dust and a catalytic amount of cuprous bromide at low temperatures in an inert solvent to give the esterified 3-hydroxypropionate derivative which is reacted directly with a substituted thiol in trifluoroacetic acid. Alternatively, a mixture of trimethyl borate and zinc in tetrahydrofuran may be used to prepare the 3-hydroxypropionate derivative. By employing an esterified 2-bromopropionate in the above reaction with an aldehyde (VI-II), the compounds of the formula (I) wherein Y is $CH(CH_3)CO_2H$ are obtained.

To prepare the compounds of formula (I) wherein q is 1 or 2, the appropriate thio product is conveniently oxidized with sodium periodate or metachloroperbenzoic acid to obtain the sulfoxide or sulfone product.

The aldehydes of the formula (VIII) are known or readily prepared utilizing the general procedures described as follows.

The aldehyde precursors to the compounds of the formula (I) wherein $R_1$ is, for example, an alkyl radical containing 8 to 13 carbon atoms are prepared from the appropriate 2-methoxyphenyl-4,4-dimethyloxazoline (see Meyers et al. *J. Org. Chem.*, 43 1372 (1978)).

The aldehyde precursors of the compounds of the formula (I) wherein $R_1$ is, for example, an alkoxy radical containing 7 to 12 carbon atoms are prepared by the O-alkylation of the appropriate 2-hydroxybenzaldehyde with the corresponding alkylating agent.

The aldehyde precursors to the compounds of the formula (I) wherein $R_1$ is a 1-alkynyl radical containing 10 to 12 carbon atoms are prepared by coupling a 2-halobenzaldehyde with the appropriate 1-alkyne in the presence of cuprous iodide and $(PO_3)_2PdCl_2$. (See Hagihara, et al. *Synthesis*, 627, (1980)). The catalytic hydrogenation of these alkynyl containing precursors under standard conditions affords the aldehyde precursors of the compounds of the formula (I) wherein $R_1$ is an alkyl or phenylalkyl radical.

The alkylthio containing aldehyde precursors of the compounds of the formula (I) are prepared by the reaction of the appropriately substituted halo alkylthio benzene with magnesium and dimethylformamide.

The phenylthioalkyl containing aldehyde precursors of the compounds of the formula (I) are prepared by the reaction of the appropriately substituted haloalkyl benzaldehyde with a thiophenol and triethylamine.

Alternately, the compounds of the formula (I) wherein Y is $CH_2CO_2H$ are prepared from a propenoate precursor of the following structural formula (IX)

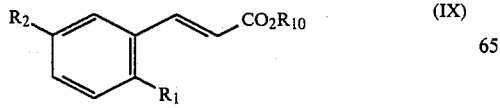

wherein $R_1$ and $R_2$ are described above, and $R_{10}$ is an ester protective group, such as t-butyl. A compound of formula (IX) is reacted with a mixture of alkali metal alkoxide, such as sodium methoxide, and substituted thiol to give, after removal of the ester protective group, products of formula (I).

The propenoate precursors of formula (IX) are prepared from the corresponding aldehydes of formula (VIII) by general procedures such as reaction with an alkyl (triphenylphosphoranylidene)acetate or by conversion of the aldehyde to a 3-hydroxypropionate derivative, as described above, followed by an elimination reaction to form the double bond. Additionally, the propenoate precursor is obtained from a 3-methanesulfonyloxypropionate derivative by treatment with triethylamine.

The compounds of the formula (I) wherein Y is $CH(OH)(CH_2)_mCO_2H$ are prepared from an epoxide precusor of the following structural formula (X)

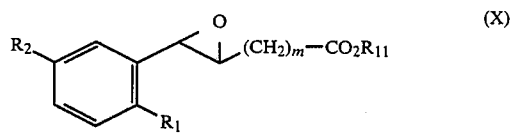

wherein $R_1$, $R_2$ and m are described above, and $R_{11}$ is lower alkyl, such as methyl or ethyl. A compound of formula (X) is reacted in an inert solvent with triethylamine and a substituted thiol selected to give, after removal of ester protective groups, a product of formula (I).

The epoxide precursors of formula (X) where m is 2 are prepared by reaction of the Grignard derivative of a bromobenzene compound of the formula (XI)

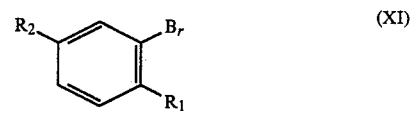

with acrolein to give the corresponding enol derivative which is treated with a trialkylorthoacetate, followed by epoxidation using metachloroperbenzoic acid.

The epoxide precursors of formula (X) where m is 0 are prepared by reaction of an aldehyde of the formula (VIII) with a lower alkyl chloroacetate and an alkali metal alkoxide, such as sodium methoxide.

Alternatively, the compounds of the formula (I) wherein Y is $CH(OH)COR_3$ are prepared from a propenoate precursor of formula (IX) wherein $R_{10}$ is lower alkyl as described more fully in the examples hereinbelow.

The compounds of the formula (I) wherein Y is $(CH_2)_3CO_2H$ are prepared from a tetrahydro-4H-pyran-2-one precursor of the following structural formula (XII)

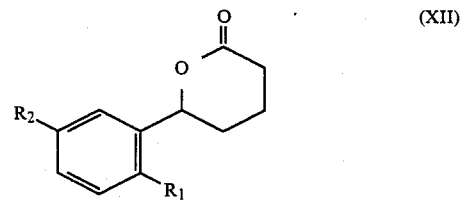

wherein $R_1$ and $R_2$ are described above. A compound of formula (XII) is reacted with a mixture of zinc iodide and a substituted thiol in an inert solvent or with a substituted thiol in trifluoroacetic acid to give, after removal of any ester protective group, a product of formula (I).

The tetrahydro-4H-pyran-2-one precursors of formula (XII) are prepared by reaction of the Grignard derivative of the bromobenzene compound of formula (XI) with chloro titanium tri-isopropoxide followed by reaction with 5-oxovalerate alkyl ester.

The 2-thioimidazole precursors necessary to prepare the R-heterocyclic derivatives of formula (I) are known compounds or are conveniently prepared employing standard chemical reactions. Preferably these reactants bearing a carboxyl or carboxymethyl substituent as set forth in $R_8$ and $R_9$ above are employed as the corresponding carboalkoxy derivatives wherein the alkoxy radical contains from one to six carbon atoms. When present, the alkoxy substitutent is subsequently hydrolyzed to give the free carboxyl or carboxymethyl substituted products.

Appropriate modifications of the general processes disclosed, and as further described in the Examples provided hereinbelow, furnish the various compounds defined by formula (I).

The leukotriene antagonist activity of the compounds of this invention is measured by the ability of the compounds to inhibit the leukotriene induced contraction of guinea pig tracheal tissues in vitro and to inhibit leukotriene induced bronchoconstriction in guinea pigs in vivo. The following methodologies were employed: In vitro: Guinea pig (adult male albino Hartley strain) tracheal spiral strips of approximate dimensions 2 to 3 mm cross-sectional width and 3.5 cm length were bathed in modified Krebs buffer in jacketed 10 ml tissue bath and continuously aerated with 95% $O_2$/5% $CO_2$. The tissues were connected via silk suture to force displacement transducers for recording isometric tension. The tissues were equilibrated for 1 hr., pretreated for 15 minutes with meclofenamic acid (1 μM) to remove intrinsic prostaglandin responses, and then pretreated for an additional 30 minutes with either the test compound or vehicle control. A cumulative concentration-response curve for $LTD_4$ on triplicate tissues was generated by successive increases in the bath concentration of the $LTD_4$. In order to minimize intertissue variability, the contractions elicited by $LTD_4$ were standardized as a percentage of the maximum response obtained to a reference agonist, carbachol (10 μM).

Calculations: The averages of the triplicate $LTD_4$ concentration-response curves both in the presence and absence of the test compound were plotted on log graph paper. The concentration of $LTD_4$ needed to elicit 30% of the contraction elicited by carbachol was measured and defined as the $EC_{30}$. The $-\log K_B$ value for the test compound was determined by the following equations:

$$\frac{EC_{30} \text{ (presence of test compound)}}{EC_{30} \text{ (presence of vehicle control)}} = \text{dose ratio} = X \quad 1.$$

$$K_B = \text{concentration of test compound}/(X - 1) \quad 2.$$

In vivo: Anesthetized, spontaneously breathing guinea pigs (Adult male albino Hartley strain) were monitored on a Buxco pulmonary mechanics computer. Changes in airway resistance ($R_L$) were calculated by the computer on a breath-by-breath basis at isovolumic points from signals measuring airflow and transpulmonary pressure using differential pressure transducers. Animals were pretreated with 1 mg/kg of propranolol, iv, followed by 100 puffs of an aqueous solution of test compound or vehicle control by aerosol via a Monaghan nebulizer. $LTD_4$ was then aerosolized into the airway. The bronchoconstriction produced was reflected by % changes in airways resistance relative to the baseline values obtained prior to injection of the test compound or vehicle control. Each guinea pig received either vehicle control or test compound.

Calculations: The average of 3-6 animals per treatment was calculated using the % changes in the pulmonary parameters for control and test compound-treated animals. The average % inhibition by the test compound was calculated from the following equation:

$$\% \text{ Inhibition} = \frac{R_L \text{ (vehicle control)} - R_L \text{ (test compound)}}{R_L \text{ (vehicle control)}} \times 100$$

The compounds of this invention possess biosignificant antagonist activity against leukotrienes, primarily leukotriene $D_4$. The antagonist activity of representative compounds of this invention is tabulated below (other data appears in the preparative examples). The $-\log K_B$ values and the $R_L$ values were calculated from the above test protocols. Where compounds were tested more than once, the $-\log K_B$ values given herein represent the current average data.

|  |  |  | In Vitro $-\log K_B$ | In Vivo Concentration | In Vivo Pretreatment Time (min) | In Vivo Inhibition of $R_L$ |
|---|---|---|---|---|---|---|
| Compounds of the Formula (III) | | | | | | |
| $R_1$ | $R_2$ | | | | | |
| $-C_8H_{16}$ phenyl | $CF_3$ | | 7.3 | 0.4% | 30 | 93% |
| $-C_8H_{16}$ phenyl | H | | 7.1 | 0.4% | 30 | 81% |
| $-C_{12}H_{25}$ | H | | 6.7 | 0.4% | 30 | 63% |
| Compounds of the Formula (IV) | | | | | | |
| $R_1$ | $R_2$ | | | | | |
| $-C_8H_{16}$ phenyl | H | | 6.6 | | | |
| $-C_{12}H_{25}$ | H | | 6.3 | 0.4% | 30 | 0% |
| Compounds of the Formula (V) | | | | | | |
| $R_1$ | $R_2$ | $R_7, R_8, R_9$ | | | | |
| $-C_{12}H_{25}$ | H | $CH_3, CO_2H$, propyl | 6.8 | | | |
| $-C_{12}H_{25}$ | H | $CH_3, CO_2H, CH_3$ | 6.7 | 1% | 5 | 61% |
| Compounds of the Formula (VI) | | | | | | |

-continued

| | | In Vitro −Log $K_B$ | In Vivo | | |
|---|---|---|---|---|---|
| | | | Concentration | Pretreatment Time (min) | Inhibition of $R_L$ |
| $R_1$ | $R_2$ | | | | |
| —$C_{12}H_{25}$ (erythro) | H | 7.8 | | | |
| —$C_8H_{16}$ phenyl (erythro) | H | 7.5 | | | |
| Compounds of the Formula (VII) | | | | | |
| $R_1$ | $R_2$ | | | | |
| —$C_{12}H_{25}$ | H tetrazol-5-yl | 6.0 | | | |
| —$C_{12}H_{25}$ | H —$CH_2$—tetrazol-5-yl | 7.4 | | | |

The specificity of the antagonist activity of a number of the compounds of this invention is demonstrated by relatively low levels of antagonism toward agonists such as potassium chloride, carbachol, histamine and $PGF_2$.

Pharmaceutical compositions of the present invention comprise a pharmaceutical carrier or diluent and an amount of a compound of the formula (I) or a pharmaceutically acceptable salt, such as an alkali metal salt thereof, sufficient to produce the inhibition of the effects of leukotrienes.

When the pharmaceutical composition is employed in the form of a solution or suspension, examples of appropriate pharmaceutical carriers or diluents include: for aqueous systems, water; for non-aqueous systems, ethanol, glycerin, propylene glycol, corn oil, cottonseed oil, peanut oil, sesame oil, liquid parafins and mixtures thereof with water; for solid systems, lactose, kaolin and mannitol; and for aerosol systems, dichlorodifluoromethane, chlorotrifluoroethane and compressed carbon dioxide. Also, in addition to the pharmaceutical carrier or diluent, the instant compositions may include other ingredients such as stabilizers, antioxidants, preservatives, lubricants, suspensing agents, viscosity modifiers and the like, provided that the additional ingredients do not have a detrimental effect on the therapeutic action of the instant compositions.

The nature of the composition and the pharmaceutical carrier or diluent will, of course, depend upon the intended route of administration, i.e. parenterally, topically, orally or by inhalation.

In general, particularly for the prophylactic treatment of asthma, the compositions will be in a form suitable for administration by inhalation. Thus the compositions will comprise a suspension or solution of the active ingredient in water for administration by means of a conventional nebulizer. Alternatively the compositions will comprise a suspension or solution of the active ingredient in a conventional liquified propellant or compressed gas to be administered from a pressurized aerosol container. The compositions may also comprise the solid active ingredient diluted with a solid diluent for administration from a powder inhalation device. In the above compositions, the amount of carrier or diluent will vary but preferably will be the major proportion of a suspension or solution of the active ingredient. When the diluent is a solid it may be present in lesser, equal or greater amounts than the solid active ingredient.

For parenteral administration the pharmaceutical composition will be in the form of a sterile injectable liquid such as an ampul or an aqueous or nonaqueous liquid suspension.

For topical administration the pharmaceutical composition will be in the form of a cream, ointment, liniment, lotion, pastes, and drops suitable for administration to the eye, ear, or nose.

For oral administration the pharmaceutical composition will be in the form of a tablet, capsule, powder, pellet, atroche, lozenge, syrup, liquid, or emulsion.

Usually a compound of formula I is administered to a subject in a composition comprising a nontoxic amount sufficient to produce an inhibition of the symptoms of a disease in which leukotrienes are a factor. When employed in this manner, the dosage of the composition is selected from the range of from 350 mg. to 1000 mg. of active ingredient for each administration. For convenience, equal doses will be administered 1 to 5 times daily with the daily dosage regimen being selected from about 350 mg. to about 5000 mg.

The pharmaceutical preparations thus described are made following the conventional techniques of the pharmaceutical chemist as appropriate to the desired end product.

Included within the scope of this disclosure is the method of treating a disease, pulmonary or non-pulmonary, in which leukotrienes are a factor which comprises administering to a subject a therapeutically effective amount of a compound of formula I, preferably in the form of a pharmaceutical composition. For example, inhibiting the symptoms of an allergic response resulting from a mediator release by administration of an effective amount of a compound of formula I is included within the scope of this disclosure. The administration may be carried out in dosage units at suitable intervals or in single doses as needed. Usually this method will be practiced when relief of symptoms is specifically required. However, the method is also usefully carried out as continuous or prophylactic treatment. It is within the skill of the art to determine by routine experimentation the effective dosage to be administered from the dose range set forth above, taking into consideration such factors as the degree of severity of the conditions or disease being treated, and so forth.

Compounds of this invention, alone and in combination with a histamine $H_1$-receptor antagonist, inhibit antigen-induced contraction of isolated, sensitized guinea pig trachea (a model of respiratory anaphylaxis). Exemplary of compounds of this invention are 2(S)-hydroxy-3(R)-(2-carboxyethylthio)-3-[2-(8-phenyloctyl)phenyl]propanoic acid (COMPOUND A) or its racemate. Exemplary of histamine $H_1$-receptor antagonists are mepyramine and 2-[4-(5-bromo-3-methylpyrid-2-yl(butylamino]-5-[(6-methylpyrid-3-yl)methyl]-4-pyrimidone (COMPOUND B). The methodologies employed and the results obtained are described as follows:

A. In Vitro Studies
 1. Guinea-pig isolated trachea. The following method employed was as described in Weichman, B. M., Wasserman, M. A., Holden, D. A., Osborn, R. R., Woodward, D. F., Ku, T. W., and Gleason, J. G., J. Pharmacol. Exp. Ther., 227, 700–705, 1983. Male adult (400–600 g) albino Hartley strain guinea-pigs were actively sensitized to ovalbumin (OA) by injecting intramuscularly 0.7 ml of a 5% OA solution. Animals responding positively to an antigen aerosol provocation 2 weeks later were selected for subsequent use after an additional 2-week wait. Normal, non-sensitized guinea pigs were used in studies where the $K_Bs$ of COMPOUND B and mepyramine were determined. Tracheas were removed, trimmed of excess tissue, cut into spiral strips, and mounted in water-jacketed 10-ml tissue baths filled with a modified Krebs-Henseleit solution maintained at 37° C. and aerated continuously with 95% $O_2$-5% $CO_2$. Tracheal strips were placed under 2.0 g of passive tension and equilibrated for 60 min, after which all tissues were treated with 1M meclofenamic acid, a cyclooxygenase inhibitor, to eliminate the formation of prostanoids. The ability of COMPOUND B to inhibit histamine-induced contraction was determined by incubating tissues with vehicle or 1, 10 or 100 nM COMPOUND B for 30 min before initiating cumulative histamine concentration-response studies. For corresponding studies with mepyramine, tissues were incubated with vehicle or 10, 100 or 1000 nM mepyramine. Cumulative concentration-response curves were constructed for each tissue by successively increasing the concentration of histamine by 10-fold increments after the maximum response to the previous concentration had been reached. All responses to histamine were standardized by adding 10M carbachol to the baths at the end of the studies. The dissociation constants ($K_Bs$) for COMPOUND B and mepyramine were determined from these data by the method of Arunlakshana and Schild (Brit. *J. Pharmacol.* 14: 48, 1959). In one set of experiments where the contractile response to antigen(OA)-challenge was determined, tissues were untreated or treated with 1 μM COMPOUND B and 1 μM COMPOUND A (alone or in combination) for 30 min before the addition of 0.01 μg/ml OA. In another set of experiments, mepyramine (10 μM) was used in place of COMPOUND B, and COMPOUND A racemate (1 μM) was used in place of COMPOUND A. The contractile response to OA was recorded for 15 min, after which the muscarinic agonist carbachol (10 μM) was added to produce maximal contaction. The contractile response to OA was calculated as a percentage of the response to the standard carbachol challenge.

2. Human isolated bronchus. Specimens of human hemilungs were removed from trauma victims at the same time donor organs for transplant were removed. Parenchymal tissue was carefully cut away from the extrapulmonary airways before sections of airway from the 2nd through 7th generation were removed. Bronchi were trimmed of excess tissue, opened longitudinally to form strips, and suspended in tissue baths. Human bronchi were passively sensitized by treatment with human IgE serum (2.8 g/ml) for 30 min. Tissues were then washed thoroughly and exposed to vehicle or to the appropriate antagonists for 30 min before being challenged with sheep anti-human IgE. In these studies, COMPOUND A racemate (10 μM) was used as the leukotriene antagonist and mepyramine (10 μM) was used as the $H_1$-receptor antagonist. Responses to antigen challenge were determined as described above for the guinea-pig isolated trachea.

B. In Vivo Studies

1. Conscious guinea pigs. The model used to test COMPOUND B, COMPOUND A racemate or mepyramine in *conscious*, OA-sensitized guinea pigs is a modification of the technique of Herxheimer in which animals are placed in an inverted 9-L glass bell jar which serves as an aerosol chamber, as described in Wasserman, M. A., Griffin, R. L., and Malo, P. E. "Proceedings of the Symposium on Inhalation Toxicology and Technology," B. Leong, ed., Ann Arbor Science Publisher, Inc., Ann Arbor, MI, pp. 247–263, 1981. The chamber is equipped with a DeVilbiss No. 40 glass nebulizer to deliver aerosols at a calculated rate of 340 l/min under a driven pressure of 5 psi. To test the effects of the various antagonists, OA-sensitized guinea pigs were placed in the aerosol chamber and exposed to an aerosolized 0.1% solution of the selected agent for 1 min. Animals were then removed from the chamber for either 59 min (Study 1) or 4 min (Study 2) before being returned and challenged with 0.1% OA aerosol. Guinea pigs received the antigen aerosol until they underwent signs and symptoms of an asthma-like bronchoconstriction (i.e., coughing and dyspnea) or until 6 min had passed, at which time the experiment was terminated. The time to the onset of dyspnea (sec) was recorded before and after pretreatment with a protective substance. Prolongation of the time to onset of dyspnea was used as an indicator of the efficacy of the antagonist. Animals were removed quickly from the chamber at the completion of the study and resuscitated as necessary.

The above in vitro studies, in the guninea-pig isolated trachea, demonstrated that both COMPOUND B (1 μM) and mepyramine (10 μM) delayed the onset of OA-induced contraction but had no effect on the ultimate maximum response. In contrast, neither COMPOUND A (1 μM) nor its racemate (1 μM) had an effect on the early phase (0–5 min) of the OA-induced contraction, but both compounds reduced the amount of force developed during the late phase (5–15 min) from 50–60% to 30–35% of that produced by carbachol. The response to OA was nearly abolished (only 10% of carbachol-induced response remained) when tissues were pretreated with either of the following two combinations: COMPOUND A (1 μM) plus COMPOUND B (1 μM) or COMPOUND A racemate (1 μM) plus mepyramine (10 μM). Similarly, in the human isolated bronchus a combination of mepyramine (10 μM) and COMPOUND A racemate (10 μM) nearly abolished the response to anti-IgE (only 15% of the carbachol-induced contraction remained).

In the above in vivo studies, in one study aerosolized COMPOUND B racemate (0.1% solution for 1 min) given 59 min prior to challenge with aerosolized OA (0.1%) increased the onset time of OA-induced dyspnea from 65 sec (control) to 180 sec (treated). Aerosolized COMPOUND B (0.1% solution for 1 min) given 60 min prior to challenge with aerosolized OA increased the onset time of OA-induced dyspnea from 65 sec (control) to 230 sec (treated); mepyramine (0.1%) increased the onset time to 105 sec. In another series of experiments, OA-sensitized guinea pigs were given a 1 min aerosol exposure to one of two combinations: COMPOUND A racemate (0.1%) plus mepyramine (0.1%) or COMPOUND A racemate (0.1%) plus COMPOUND B (0.1%). Four min after the pretreatment, animals were challenged with aerosolized OA (0.1%). In these experiments, the first combination increased the onset time of OA-induced dyspnea from 60 sec (control) to 190 sec (treated); the second combination was much more effective, increasing the time of onset to 340 sec.

Pharmaceutical compositions, as described hereinabove, of the present invention also comprises a pharmaceutical carrier or diluent and a combination of a compound of the formula (I) or a pharmaceutically acceptable salt thereof, and an histamine $H_1$-receptor antagonist in amounts sufficient to inhibit antigen-induced respiratory anaphylaxis. The above-defined dosage of a compound of formula I is conveniently employed for this purpose and the known effective dosage for the histamine $H_1$-receptor antagonist. The methods of administration described above for the single active ingredient can similarly be employed for the combination with a histamine $H_1$-receptor antagonist.

The following examples illustrate the preparation of the compounds of this invention and their incorporation into pharmaceutical compositions and as such are not to be considered as limiting the invention set forth in the claims appended hereto.

EXAMPLE 1

Preparation of 2-(Carboxymethylthio)-2-(2-dodecylphenyl) acetic acid (a) 2-(2-Dodecylphenyl)-4,4-dimethyloxazoline To freshly prepared dodecylmagnesium bromide (from 30.13 mmoles of dodecyl bromide and 26.20 mmoles of magnesium) in distilled tetrahydrofuran (50 ml) was added 2-(2-methoxyphenyl)-4,4-dimethyloxazoline (A. I. Meyers et al., *J. Org. Chem.*, 43, 1372 (1978)) (17.88 mmoles) in tetrahydrofuran (30 ml). The resultant yellow solution was stirred under argon at ambient temperature for 20 hours. The solution was cooled in an ice water bath and quenched with aqueous ammonium chloride (100 ml). The reaction product was extracted into diethyl ether (100 ml) and the organic phase was washed with saturated sodium chloride solution (50 ml) and then dried over anhydrous magnesium sulfate. Evaporation of the organic phase afforded a colorless oil which was purified by flash chromatography over silica gel with 5 percent ethyl acetate in hexane as eluant to afford the desired product as a pale yellow oil.

Analysis for $C_{23}H_{37}NO$: Calculated: C, 80.41; H, 10.85; N, 4.08. Found: C, 80.22; H, 10.56; N, 3.87.

(b) 2-(2-Dodecylphenyl)-3,4,4-trimethyloxazolinium iodide

A solution of the compound of Example 1(a) (17.2 mmoles) in methyl iodide (20 ml) was refluxed under argon for 18 hours. The volatiles were removed under vacuum and the solid residue triturated with ethyl acetate (25 ml) to afford the desired product as white crystals (mp 78°-84° C.).

(c) 2-Dodecylbenzaldehye

To an ice cold solution of the compound of Example 1(b) (10.0 mmoles) in methanol (50 ml) over a period of 15 minutes was added in small portions sodium borohydride (10.0 mmoles). The reaction mixture was allowed to stir for 30 minutes and was then quenched with 5 percent sodium hydroxide (50 ml). The reaction mixture was extracted with diethyl ether (2×50 ml) and the extract was washed with brine (50 ml) and dried over anhydrous magnesium sulfate. Evaporation of the extract afforded an oil which was dissolved in acetone (50 ml) and 3N hydrochloric acid (10 ml) was added. The mixture was flushed with argon and stirred for 16 hours at ambient temperature. The volatiles were removed under vacuum and the residue partitioned between diethyl ether (50 ml) and water (50 ml). The aqueous phase was extracted with more diethyl ether (50 ml). The combined organic phase was washed with brine (50 ml) and dried over anhydrous magnesium sulfate. Evaporation of the organic phase yielded an oil which was purified by flash chromatography over silica gel with 2 percent ethyl acetate in hexane as eluant to afford the desired product as a colorless oil.

Analysis for $C_{19}H_{30}O$: Calculated: C, 83.15; H, 11.02. Found C, 82.59; H, 10.65.

Alternatively, the compound of Example 21(a) is hydrogenated in the presence of 10% palladium-on-charcoal (see Example 7b) to give 2-dodecylbenzaldehyde.

(d) Methyl 2-(2-dodecylphenyl)-2-hydroxy acetate

The compound of Example 1(c) (17.2 mmoles) was dissolved in methylene chloride (20 ml) and stirred at 0° C. under argon. Zinc iodide (1.87 mmoles) was added, followed by the dropwise addition of trimethylsilyl cyanide (2.45 ml, 18.3 mmoles) dissolved in methylene chloride (30 ml). After 1 hour at 0° C. the ice bath was removed and the mixture stirred for 1 hour at room temperature. The solvent was stripped and methanol (100 ml) was added after the residue was cooled in an ice bath. Excess hydrogen chloride was bubbled into the solution while the mixture was stirred at ice bath temperature. The ice bath was then removed and the mixture stirred at room temperature for 18 hours. Water (20 ml) was added and the mixture stirred for 2 hours. The solvent was evaporated and the aqueous residue extracted with ethyl acetate. The combined organic phases were dried over anhydrous sodium sulfate, filtered and evaporated. The crude product was flash chromatographed on silica gel, eluted with 20% ethyl acetate/hexane, to give the product as a clear colorless liquid.

(e) Methyl 2-Chloro-2-(2-dodecylphenyl)acetate

The compound of Example 1(d) (12 mmoles) was stirred under argon in an ice bath and thionyl chloride (20 ml) was added in a single portion. The ice bath was removed and the mixture was stirred under argon for 18 hours. The solvent was stripped and the residue flash chromatographed on 200 grams of silica gel eluted with 20% methylene chloride/carbon tetrachloride to give the product as a clear colorless liquid.

(f) Methyl 2-(Carbomethoxymethylthio)-2-(2-dodecylphenyl)acetate

The compound of Example 1(e) (1.42 mmoles) was dissolved in methylene chloride (5 ml) and the mixture stirred at 0° C. under argon. Methyl thioglycolate (4.26 mmoles) was added, followed by triethylamine (1.56 mmoles). The ice bath was removed and the mixture stirred at room temperature for 2.5 hours. The solvent was evaporated and the residue flash chromatographed on 50 grams of silica gel eluted with 5–10% ethyl acetate/hexane to give the product as a clear colorless liquid.

(g) 2-(Carboxymethylthio)-2-(2-dodecylphenyl)acetic acid

The compound of Example 1(f) (0.9 mmole) was dissolved in methanol (7.2 ml) and stirred under argon in an ice-bath. A 1N solution of sodium hydroxide (3.6 ml, 3.6 mmoles) was added dropwise and the ice bath removed. After 2 hours at room temperature, the methanol was stripped, water (15 ml) was added and the mixture warmed to 45° C. After an additional 2 hours at room temperature, methanol (15 ml) was added. The mixture was stirred for 18 hours and then stripped. The residue was cooled in an ice bath, acidified with hydrochloric acid, extracted with ethyl acetate, dried over anhydrous sodium sulfate, filtered and evaporated. The crude product was recrystallized twice from hexane-ethyl acetate, and a final recrystallization from hexane gave the desired product as a white crystalline solid, mp 65°–66° C., $-\log K_B$ value 5.4.

Analysis for $C_{22}H_{34}O_4S$: Calculated: C, 66.97; H, 8.69; S, 8.13. Found: C, 67.01; H, 8.58; S, 8.32.

Similarly, the following compounds are prepared according to the general methods of Examples 1 from the 2-(2-methoxyphenyl)-4,4-dimethyloxazoline and the appropriate alkyl halide:

2-(Carboxymethylthio)-2-(2-decylphenyl) acetic acid; and 2-(Carboxymethylthio)-2-(2-octylphenyl) acetic acid.

EXAMPLE 2

Preparation of 2-(2-Carboxyethylthio)-2-(2-dodecylphenyl)acetic acid (a) Methyl 2-(2-carbomethoxyethylthio)-2-(2-dodecylphenyl)acetate The compound of Example 1(e) (3.04 mmoles) was dissolved in methylene chloride (10 ml) and stirred under argon at 0° C. Methyl 3-mercaptopropionate (3.3 mmoles) and triethylamine (3.3 mmoles) in methylene chloride (5 ml) was added dropwise over 5 minutes. The ice-bath was removed and the mixture stirred under argon at room temperature for 2.5 days. Flash chromatography on 100 grams of silica gel eluted with 10% ethyl acetate/hexane gave the product as a clear colorless liquid.

(b) 2-(2-Carboxyethylthio)-2-(2-dodecylphenyl)acetic acid

The compound of Example 2(a) (1.95 mmoles) was dissolved in methanol (16 ml) and cooled to 0° C. while stirring under argon. A 1N solution of sodium hydroxide (8 ml, 8 mmoles) was added dropwise over a period of 1 minute. The ice bath was removed and the mixture stirred for 18 hours. The methanol was stripped and the residue cooled in an ice bath and acidified with hydrochloric acid. The crude product was extracted with ethyl acetate, dried over anhydrous sodium sulfate, filtered and evaporated. The product was first crystallized from hexane containing a trace of ethyl acetate and then recrystallized again from hexane to give the desired product as a white crystalline solid, mp 44°–46° C.

Analysis for $C_{23}H_{36}O_4S$: Calculated: C, 67.61; H, 8.88; S, 7.85. Found: C, 67.51; H, 8.94; S, 7.75.

EXAMPLE 3

Preparation of 2-(2-Dodecylphenyl)-2-(1,4-dimethyl-5-carboxy-2-imidazolylthio)acetic acid (a) Methyl 2-(2-dodecylphenyl)-2-(1,4-dimethyl-5-carbethoxy-2-imidazolylthio)acetate The compound of Example 1(e) (1 mmole), triethylamine (1.5 mmoles) and 1,4-dimethyl-2-mercapto-5-carbethoxyimidazole (1.33 mmoles) were dissolved in methylene chloride (25 ml) and stirred for 18 hours under argon. The solvent was stripped and the residue flash chromatographed on 50 grams of silica gel eluted with 15% ethyl acetate/hexane to give the product.

(b) 2-(2-Dodecylphenyl)-2-(1,4-dimethyl-5-carboxy-2-imidazolythio)acetic acid

The compound of Example 3(a) (0.87 mmole) was dissolved in methanol (10.5 ml) and stirred under argon at 0° C. A 1N solution of sodium hydroxide (5.2 ml, 5.2 mmoles) was added dropwise and the mixture stirred under argon at room temperature for 44 hours. The methanol was stripped off and the residue diluted with water, cooled in an ice bath and the pH adjusted to 4.0 with hydrochloric acid. The product was extracted with ethyl acetate, dried over anhydrous sodium sulfate, filtered and evaporated. The crude product was recrystallized from ethyl acetate/hexane to give the desired product as a white crystalline solid, mp 104°–106° C.

Analysis for $C_{26}H_{38}N_2O_4S$: Calculated: C, 65.79; H, 8.07; N, 5.90; S, 6.75. Found C, 65.44; H, 8.13; N, 5.76; S, 6.68.

The following compounds are prepared by utilizing the general procedures of Example 3(a) and 3(b) from the appropriate starting materials:

2-(2-Dodecyphenyl)-2-(1-methyl-2-imidazolylthio)acetic acid;

2-(2-Dodecylphenyl)-2-(1-methyl-5-carboxamido-2-imidazolylthio)acetic acid;

2-(2-Dodecylphenyl)-2-(1-ethyl-2-imidazolylthio)acetic acid;

2-(2-Dodecylphenyl)-2-(1-allyl-2-imidazolylthio)acetic acid; and 2-(2-Dodecylphenyl-2-(1,4,5-trimethyl-2-imidazolylthio)acetic acid.

EXAMPLE 4

Preparation of 3-Aza-4-oxo-7-thia-8-(2-dodecylphenyl)nonanedioic acid (a) 3-Aza-4-oxo-7-thia-8-(2-dodecylphenyl)nonanedioic acid dimethyl ester The compound of Example 1(e) (1.5 mmoles), methyl 3-aza-4-oxo-6-mercaptohexanoate (2.0 mmoles), and triethylamine (2.0 mmoles) were dissolved in methylene chloride (25 ml) and stirred under argon at room temperature for 5 days. The solvents were stripped and the residue flash chromatographed on 50 grams of silica gel eluted with 50% ethyl acetate/hexane to give the product.

(b) 3-Aza-4-oxo-7-thia-8-(2-dodecylphenyl)nonanedioic acid

The compound of Example 4(a) (0.81 mmole) was dissolved in methanol (6.5 ml) and stirred under argon at 0° C. A 1N solution of sodium hydroxide (3.25 ml, 3.25 mmoles) was added dropwise and the ice bath removed. The mixture was stirred at room temperature under argon for 21 hours. The methanol was stripped, the residue diluted with water, cooled in an ice bath, and acidified with hydrochloric acid. The product was extracted with ethyl acetate, dried over anhydrous sodium sulfate, filtered, and evaporated. The crude product was recrystallized from ethyl acetate/hexane to give the desired product, mp 105.5°–107° C., $-\log K_B$ value 6.4.

Analysis for $C_{25}H_{39}NO_5S \cdot \frac{3}{8}H_2O$: Calculated: C, 63,56; H, 8.48; N, 2.97; S, 6.79. Found: C, 63.50; H, 8.32; N, 2.89; S, 6.51.

EXAMPLE 5

Preparation of 2-(2-Dodecylphenyl)-2-(1-methyl-4-propyl-5-carboxy-2-imidazolylthio)acetic acid (a) Methyl 2-(2-dodecylphenyl)-2-(1-methyl-4-propyl-5-carbethoxy-2-imidazolylthio)acetate The compound of Example 1(e) (1 mmole), 1-methyl-2-mercapto-4-propyl-5-carbethoxyimidazole (1.33 mmoles), and triethylamine (1.5 mmoles) were dissolved in methylene chloride (25 ml) and stirred under argon at room temperature for 18 hours. The reaction mixture was warmed to reflux for 8 hours and then stirred at room temperature for 18 hours. The solvents were stripped and the residue flash chromatographed on 50 grams of silica gel eluted with 10% ethyl acetate/hexane to give the product as a clear colorless oil.

(b) 2-(2-Dodecylphenyl)-2-(1-methyl-4-propyl-5-carboxy-2-imidazolylthio)acetic acid The compound of Example 5(a) (0.94 mmole) was dissolved in methanol (11.2 ml) and stirred under argon at 0° C. A 1N solution hydroxide (5.6 ml, 5.6 mmoles) was added dropwise and the mixture stirred for 18 hours at room temperature. The mixture was warmed to 45° C. for 7 hours, with stirring under argon, and then stirred at room temperature for 18 hours. The pH was adjusted to 3.97 with dilute hydrochloric acid and the product extracted with ethyl acetate, dried over anhydrous sodium sulfate, filtered and evaporated. The crude product was recrystallized from ethyl acetate/hexane to give the desired product as a white crystalline solid, mp 124°–125° C.

Analysis for $C_{28}H_{42}N_2O_4S$: Calculated: C, 66.90; H, 8.42; N, 5.57; S, 6.38. Found: C, 66.82; H, 8.40; N, 5.52; S, 6.68.

EXAMPLE 6

Preparation of 2-(3-Carboxypropylthio)-2-(2-dodecylphenyl)acetic acid (a) Methyl 2-(3-Carboxypropylthio)-2-(2-dodecylphenyl)acetate The compound of Example 1(e) (1 mmole), 4-mercaptobutyric acid (1.33 mmoles), and triethylamine (3 mmoles) were dissolved in methylene chloride (25 ml) and stirred at room temperature under argon for 5 days. The solvents were pumped off and the residue flash chromatographed on 50 grams on silica gel eluted with 6:3:1 methylene chloride:ethanol:ammonium hydroxide. The eluant was concentrated, acidified with hydrochloric acid, extracted with ethyl acetate, dried over anhydrous sodium sulfate, filtered and evaporated to give the product.

(b) 2-(3-Carboxypropylthio)-2-(2-dodecylphenyl)acetic acid

The compound of Example 6(a) (0.34 mmole) was dissolved in methanol (3 ml) and stirred under argon at 0° C. A 1N solution of sodium hydroxide (1 ml, 1 mmole) was added dropwise and the ice bath removed. The mixture was stirred for 18 hours at room temperature. The solvent was stripped and the residue cooled in an ice bath and acidified with hydrochloric acid. The crude product was extracted with ethyl acetate, dried over anhydrous sodium sulfate, filtered and evaporated. The desired product was obtained, after recrystallization from hexane containing a trace of ethyl acetate, as a white crystalline solid, mp 58°–59° C., $-\log K_B$ value 6.8.

Analysis for $C_{24}H_{38}O_4S$ (0.15 mole $H_2O$): Calculated: C, 67.77; H, 9.08. Found: C, 67.80; H, 9.37.

EXAMPLE 7

Preparation of 2-(2-Carboxyethylthio)-2-[2-(8-phenyloctyl)phenyl]acetic acid (a) 2-(8-Phenyloctyl)benzaldehyde Following the procedures of Example 1(a), (b) and (c), to 8-phenyloctylmagnesium bromide (from 24.25 mmoles of 8-phenyloctyl bromide and 21.27 mmoles of magnesium) in distilled tetrahydrofuran (40 ml) was added 2-(2-methoxyphenyl)-4,4-dimethyloxazoline (17.10 mmoles) in tetrahydrofuran (20 ml). (The 8-phenyloctyl bromide was prepared from 8-phenyloctanol, carbon tetrabromide and triphenylphosphine in methylene chloride analogous to the procedure described in Example 22(a).) After stirring for 24 hours, the reaction mixture was similarly worked up to yield 2-[2-(8-phenyloctyl)phenyl]-4,4-dimethyloxazoline as an oil. A solution of the oxazoline (11.58 mmoles) in methyl iodide (20 ml) was refluxed under argon for 18 hours. Removal of the volatiles afforded the corresponding 3,4,4-trimethyloxazolinium iodide as a white solid (mp 76.5°–78° C). To an ice cold solution of the iodide (9.46 mmoles) in methanol (35 ml) was added in portions sodium borohydride (9.20 mmoles). Treatment of the reaction mixture as in Example 1(c) results in the isolation of the desired product as an oil.

Analysis for $C_{21}H_{26}O$: Calculated: C, 85.67; H, 8.90. Found: C, 85.12, 85.22; H, 8.94, 8.96.

(b) Alternative preparation of 2-(8-phenyloctyl)benzaldehyde

A solution of 5-hexynyl alcohol (102 mmoles) in pyridine (150 ml), under argon, was cooled to 0° C. and p-toluenesulfonyl chloride (204 mmoles) was added. The reaction mixture was kept at about 4° C. for 18 hours, poured into ice-water and then taken up in ether. The ether extract was washed with cold 10% hydrochloric acid, water and brine. The organic layer was dried and concentrated in vacuo to give 5-hexynyl p- toluenesulfonate. A solution of phenylacetylene (97 mmoles) in tetrahydrofuran (200 ml) containing a trace of triphenylmethane was cooled to 0° C. and then n-butyl lithium (37.3 ml of 2.6 moles in hexane) was added dropwise. The resulting solution was stirred at 0° C. for 10 minutes and hexamethylphosphoramide (21 ml) was added dropwise. After stirring for 10 minutes a solution of 5-hexynyl p-toluenesulfonate (97.1 mmoles) in tetrahydrofuran (200 ml) was added. The reaction mixture was stirred at room temperature for 18 hours, diluted with ether and the organic layer was washed with water and brine. The dried organic solution was concentrated and the product was purified by flash chromatography to give 1-phenylocta-1,7-diyne. A mixture of this compound (43 mmoles), 2-bromobenzaldehyde (35.8 mmoles), cuprous iodide (0.5 mmoles) and bis(triphenylphosphine) palladium (II) chloride (0.7 mmoles) in triethylamine (100 ml) was heated in an oil bath (95° C.) for one hour. The reaction mixture was cooled to 0° C., filtered and the filtrate was concentrated. The residue was dissolved in ether, washed with 10% hydrochloric acid, water and brine. The organic layer was dried and concentrated to give a product which was purified by flash chromatography to yield 2-(8-phenyl-1,7-octadiynyl)benzaldehyde. A solution of this compound (24.1 mmoles) in ethyl acetate (100 ml) and 10% palladium on charcoal (1 g) was hydrogenated (40 psi of hydrogen) at room temperature for 15 minutes. The catalyst was filtered off and the filtrate concentrated to give the 2-(8-phenyloctyl)benzaldehyde.

(c) Methyl 2-[2-(8-phenyloctyl)phenyl]-2-hydroxy acetate

The compound of Example 7(a) or 7(b) (10 mmoles) was dissolved in methylene chloride (10 ml) and stirred at 0° C. under argon. Zinc iodide (1.1 mmoles) was added followed by the dropwise addition of trimethylsilyl cyanide (1.47 ml, 11 mmoles) dissolved in methylene chloride (20 ml). After 1 hour at 0° C. the ice bath was removed and the mixture stirred for 1 hour at room temperature. The solvent was stripped and methanol (60 ml) was added at ice bath temperature. Excess hydrogen chloride was bubbled into the solution while stirring. The ice bath was removed and the mixture stirred at room temperature for 18 hours. Water (12 ml) was added and the mixture stirred for 2 hours. The solvent was evaporated and the residue extracted with ethyl acetate, dried over anhydrous sodium sulfate, filtered and evaporated. The crude product was flash chromatographed on 200 grams of silica gel eluted with 20% ethyl acetate/hexane to give the product as a clear colorless liquid.

(d) Methyl 2-chloro-2-[2-(8-phenyloctyl)phenyl]acetate

The compound of Example 7(c) (6.8 mmoles) was stirred under argon in an ice bath and thionyl chloride (15 ml) was added in a single portion. The ice bath was removed and the reaction mixture was stirred for 18 hours. The solvent was stripped and the residue flash chromatographed on 100 grams of silica gel eluted with 20% methylene chloride/carbon tetrachloride to give the product as a clear colorless liquid.

(e) Methyl 2-(2-carbomethoxyethylthio)-2-[2-(8-phenyloctyl)phenyl]acetate

The compound of Example 7(d) (5.4 mmoles), methyl 3-mercaptopropionate (5.9 mmoles), and triethylamine (5.9 mmoles) were dissolved in methylene chloride (30 ml) and stirred under argon at room temperature for 5 days. The solvents were stripped and the residue was flash chromatographed on 100 grams of silica gel eluted with 10% ethyl acetate/hexane to give the product as a clear colorless liquid.

(f) 2-(2-Carboxyethylthio)-2-[2-(8-phenyloctyl)phenyl] acetic acid

The compound of Example 7(e) (3.3 mmoles) was dissolved in methanol (25 ml) and stirred under argon at 0° C. A 1N solution of sodium hydroxide (13.2 ml, 13.2 mmoles) was added and the ice bath removed. The mixture was stirred for 18 hours at room temperature. The methanol was stripped and the residue acidified with hydrochloric acid at 0° C. The crude product was extracted with ethyl acetate, dried over anhydrous sodium sulfate, filtered, and evaporated. The product was recrystallized twice from hexane containing a trace of ethyl acetate to give the desired product as a white crystalline solid, mp 86°–87° C.

Analysis for $C_{25}H_{32}O_4S$: Calculated: C, 70.06; H, 7.53. Found: C, 69.72; H, 7.47.

EXAMPLE 8

Preparation of 2-(2-Carboxamidoethylthio)-2-(2-dodecylphenyl)acetic acid (a) 3-Mercaptopropionamide To a suspension of 3,3'-dithiodipropionic acid (0.04 mole) in chloroform (250 ml) was added thionyl chloride (21 ml) and 4 drops of dimethylformamide. The mixture was heated under reflux for one hour and allowed to stand at room temperature for 18 hours. The reaction mixture was concentrated in vacuo and azeotroped with toluene. The residual oil (acid chloride) was dissolved in a small amount of ether and added to cold concentrated ammonium hydroxide (25 ml) dropwise, with stirring. The stirring was continued for 15 minutes. The mixture was filtered and washed with a large volume of cold water. A white solid was obtained which was oven-dried to give 3,3'-dithiodipropionamide, mp 178°–180° C. To a solution of this amide (28.8 mmoles) in acetone (200 ml) was added tri-n-butylphosphine (63.5 mmoles) followed by water (200 ml). This mixture was stirred at room temperature for 18 hours. The reaction mixture was concentrated in vacuo, azeotroped with excess toluene and the residual oil was treated with ether. The separated solid was filtered, redissolved in methylene chloride, dried over magnesium sulfate, filtered and concentrated to give the solid product, mp 100°–101° C.

(b) Methyl 2-(2-Carboxamidoethylthio)-2-(2-dodecylphenyl)acetate

To a solution of the compound of Example 1(e) (1 mmole) and the compound of Example 8(a) (1.33 mmoles) in methylene chloride (10 ml) was added triethylamine (1.5 mmoles) and the mixture was stirred at room temperature for 48 hours. The reaction mixture was washed with water, 5% potassium carbonate solution and water, dried and concentrated. The residual oil solidified upon cooling and trituration with ether to give the product, mp 119°–120° C.

(c) 2-(2-Carboxamidoethylthio)-2-(2-dodecylphenyl)acetic acid

To a solution of the compound of Example 8(b) (0.446 mmole) in methanol (5 ml) was added 3M potassium carbonate (5 ml) and the mixture was stirred for 48 hours. The reaction mixture was concentrated in vacuo and the solid residue was redissolved in water. The pH was adjusted with dilute phosphoric acid until a solid separated. The solid was extracted into ethyl acetate, washed with water, dried and concentrated. Trituration with petroleum ether gave the desired product, mp 117°–119° C., $-\log K_B$ value 5.8.

Analysis for $C_{23}H_{37}NO_3S$: Calculated: C, 67.77; H, 9.15; N, 3.44. Found: C, 67.89; H, 9.09; N, 3.51.

EXAMPLE 9

Preparation of 3-(2-Carboxyethylthio)-3-(2-dodecylphenyl)propanoic acid (a) t-Butyl 3-hydroxy-3-(2-dodecylphenyl)propionate A solution of diethylaluminum chloride (54.7 mmoles) in hexane was added to a slurry of zinc dust (74.5 mmoles) and a catalytic amount of copper (I) bromide (2.5 mmoles) in anhydrous tetrahydrofuran (300 ml) while stirring under argon at 20° C. The resulting mixture was cooled to 0° C. in an ice-methanol bath. A solution of t-butyl bromoacetate (49.8 mmoles) and the compound of Example 1(c) (54.7 mmoles) in anhydrous tetrahydrofuran was added slowly over 60 minutes at 0° C. The mixture was stirred for 24 hours and then allowed to warm to room temperature. The mixture was filtered to remove zinc, concentrated, acidified with 3N hydrochloric acid and extracted with ether. Organic extracts were dried over magnesium sulfate, filtered and evaporated to afford crude product. This material was flash chromatographed using 8% ethyl acetate in hexane to give the product.

(b) 3-(2-Carboxyethylthio)-3-(2-dodecylphenyl)propanoic acid

To trifluoroacetic acid (80 ml), cooled to 0° C. in an ice-methanol bath, was added 3-mercaptopropionic acid (25.6 mmoles), followed by the compound of Example 9(a) (12.8 mmoles) in methylene chloride (20 ml). The mixture was stirred at 0° C. under argon for 24 hours. The reaction mixture was concentrated, the residue was dissolved in carbon tetrachloride and washed with water. The organic phase was dried over magnesium sulfate, filtered and evaporated to give the crude product. This was recrystallized from hexane to afford the desired product, mp 55°–56° C.

Analysis for $C_{24}H_{38}O_4S$: Calculated: C, 68.21; H, 9.06; S, 7.59. Found: C, 68.01; H, 9.03; S, 7.35.

EXAMPLE 10

Alternative Preparation of 3-(2-Carboxyethylthio)-3-(2-dodecylphenyl)propanoic acid (a) t-Butyl 3-(2-dodecylphenyl)propenoate The compound of Example 1(c) (32 mmoles) was dissolved in toluene (50 ml) and cooled to 0° C. in an ice-water bath while stirring under argon. t-Butyl (triphenylphosphoranylidene)acetate (32 mmoles) was added in one portion. The mixture was heated at 110° C. for 24 hours. The toluene was evaporated and the resulting residue was flash chromatographed using a 6% ethyl acetate in hexane system to give the product.

(b) t-Butyl 3-(2-carboxyethylthio)-3-(2-dodecylphenyl)propionate

Sodium (155.5 mmoles) was added slowly to methanol (200 ml) under an atmosphere of argon. The mixture was cooled to 0° C. in an ice bath and 3-mercaptopropionic acid (78 mmoles) was added dropwise. This mixture was stirred for 30 minutes and the compound of Example 10(a) (7.8 mmoles) was added dropwise. The reaction mixture was stirred for 24 hours. The solvent was evaporated. The residue was taken up in ice water and acidifed with 10% phosphoric acid to a pH of 6.5. The product was extracted into ethyl acetate. The combined organic extracts were dried over magnesium sulfate, filtered and evaporated. The resulting residue was flash chromatographed with 1.0% methanol and 1.0% formic acid in methylene chloride. This provided the product as an oil.

(c) 3-(2-Carboxyethylthio)-3-(2-dodecylphenyl)propanoic acid

To the compound of Example 10(b) (5.6 mmoles), cooled to $-10°$ C. with an ice-methanol bath, was added cold trifluoroacetic acid (10–15 ml). The mixture was stirred under argon for 2.5 hours. Evaporation gave a solid which was recrystallized from diethyl ether-hexane to give the desired product, mp 55°–56° C., identical to the product of Example 9.

EXAMPLE 11

Preparation of 3-Aza-4-oxo-7-thia-8-(2-dodecylphenyl)decanedioic acid (a) di-(t-Butyl) 3-aza-4-oxo-7-thia-8-(2-dodecylphenyl)decanedioate A mixture of the compound of Example 10(b) (1.3 mmoles) and methylene chloride (4 ml) was cooled to 0° C. in an ice-methanol bath under argon. To this mixture was added glycine t-butyl ester (1.3 mmoles) in methylene chloride (4 ml) and 1,3-dicyclohexylcarbodiimide. The ice bath was removed and the reaction was stirred for 24 hours. The reaction mixture was filtered, then concentrated. The resulting residue was flash chromatographed on silica eluted with 20% ethyl acetate in hexane to afford the product.

(b) 3-Aza-4-oxo-7-thia-8-(2-dodecylphenyl)decanedioic acid

A mixture of the compound of Example 11(a) (0.609 mmole) and methylene chloride (2.0 ml) was cooled to 0° C. in an ice-methanol bath. Trifluoroacetic acid (70 ml) was added and the mixture was stirred for 6 hours under argon. The mixture was warmed to 15° C. for 30 minutes and then evaporated. The residue was flash chromatographed on silica eluted with 20% ethyl acetate in hexane to give the desired product, mp 64°–65° C., $-\log K_B$ value 6.4.

Analysis for $C_{26}H_{41}NO_5S$: Calculated: C, 65.10; H, 8.62; N, 2.92; S, 6.68. Found: C, 64.86; H, 8.71; N, 2.84; S, 6.80.

EXAMPLE 12

Preparation of
2-Methyl-3-(2-carboxyethylthio)-3-(2-dodecylphenyl)-propanoic acid (a) Methyl
2-methyl-3-hydroxy-3-(2-dodecylphenyl)propanoate To a suspension of zinc dust (15 mmoles) and copper (I) bromide (5 mmoles) in distilled tetrahydrofuran (10 ml) at 25° C. was added diethylaluminum chloride (10 mmoles). The mixture was stirred for 5 minutes, then cooled to 0° C. in an ice-methanol bath. A solution of the compound of Example 1(c) (10 mmoles) and methyl d,1-2-bromopropionate (10 mmoles) in tetrahydrofuran (10 ml) was added dropwise to the cold suspension. The resulting mixture was stirred for 3 hours at 25° C. The reaction mixture was filtered and the filtrate was washed with water, dried over magnesium sulfate, and evaporated to give the product.

(b) Methyl
2-methyl-3-(2-carboxyethylthio)-3-(2-dodecylphenyl)-propanoate

To a solution of trifluoroacetic acid (15 ml) and 3-mercaptopropionic acid (2.4 ml) at 0° C. was added the compound of Example 12(a). The reaction mixture was stirred for 3 hours and evaporated. The resulting residue was flash chromatographed on silica, eluted with 20% ethyl acetate in hexane, to give a mixture of erythro and threo isomers of the product.

(c)
2-Methyl-3-(2-carboxyethylthio)-3-(2-dodecylphenyl)-propanoic acid

To a solution of 10% sodium hydroxide (50 ml), methanol (12 ml) and ethylene glycol dimethyl ether was added the mixture of compounds of Example 12(b) (93.9 mmoles). The mixture was stirred for 24 hours at 25° C. The reaction mixture was then cooled in an ice-methanol bath to 0° C. and acidified with hydrochloric acid to pH 3.5, extracted with diethyl ether, dried over magnesium sulfate, filtered and evaporated. The resulting mixture of isomers was flash chromatographed on silica, eluted with 30% ethyl acetate in hexane, to give a 4:1 mixture of threo and erythro iosmers.

Analysis for $C_{25}H_{40}O_4S$: Calculated: C, 68.77; H, 9.23. Found for isomer A (erythro)*: C, 68.59; H, 9.29. Found for isomer B (threo)*: C, 68.30; H, 9.23. Isomer A $-\log K_B$ value 6.4; isomer B $-\log K_B$ value 5.5.
*Assignments based on following reference: J. Canceill, J-J Basseller and J. Jacques, Bull. Soc. Chim., 1967, 1024.

EXAMPLE 13

Preparation of
3-(2-Carboxyethylthio)-3-[2-(8-phenyloctyl)phenyl]-propanoic acid (a) t-Butyl
3-[2-(8-phenyloctyl)phenyl]-3-hydroxypropanoate The compound of Example 7(a) or 7(b) (6.79 mmoles) in tetrahydrofuran (7 ml) and trimethyl borate (7 ml) were added dropwise with stirring to zinc metal (8.8 mmoles) at 25° C. After 5 minutes, t-butyl bromoacetate (6.79 mmoles) was added all at once and the mixture was stirred for 24 hours. An additional 2 ml. of t-butyl bromoacetate was added and the mixture stirred at room temperature for 36 hours. The reaction mixture was diluted with ether, cooled to 0° C., and ice-cold ammonium hydroxide/water/glycerine was added dropwise with stirring. The organic layer was washed with water and brine, dried over magnesium sulfate and concentrated. The residue was flash chromatographed on silica, eluted with 5% ethyl acetate/hexane, to give the product as a clear colorless oil.

Analysis for $C_{27}H_{38}O_3$: Calculated: C, 78.98; H, 9.33. Found: C, 79.09; H, 9.33.

(b)
3-(2-Carboxyethylthio)-3-[2-(8-phenyloctyl)phenyl]-propanoic acid

The compound of Example 13(a) (5.5 mmoles) was dissolved in methylene chloride (25 ml), under argon, the solution was cooled to $-15°$ C. and 3-mercaptopropionic acid (16.6 mmoles) was added. Trifluoroacetic acid (25 ml.) was added dropwise over 30 minutes. The reaction mixture was maintained at $-15°$ C. for 30 minutes and then the temperature was allowed to rise to 0° C. for 5 hours. The mixture was stirred for 2 hours and then concentrated in vacuo at 0° C. The residue was redissolved in methylene chloride, washed with water until neutral, dried and concentrated. The resultant oil was flash chromatographed on silica, eluted with 20% ethyl acetate/hexane/0.5% formic acid. The appropriate fractions were combined, concentrated, taken up in methylene chloride, washed with water until neutral, dried and concentrated. This oil was flash chromatographed on silica, eluted with 15% ethyl acetate/hexane/0.5% formic acid, to give the desired product as an oil. The oil (1.1477 mmoles) was swirled with aqueous potassium carbonate (9.6 ml, 2.869 mmoles) for 20 minutes. The solution was stirred for one hour at room temperature and then flash chromatographed, on a reverse phase support, being eluted with 50:50 acetonitrile/water, to give after lyophilization the dipotassium salt, mp 270° C. (dec.).

Analysis for $C_{26}H_{32}SO_4K_2\frac{3}{4}H_2O$: Calculated: C, 58.67; H, 6.34; S, 6.02. Found: C, 58.73; H, 6.13; S, 6.25.

The disodium, dimagnesium and dicalcium salts of the above copound are prepared by the general methods.

EXAMPLE 14

Preparation of
3-(2-Carboxyethylthio)-3-[2-(8-phenyloctyl)-5-trifluoromethylphenyl]propanoic acid (a) 2-(8-Phenyloctyl)-5-trifluoromethyl benzaldehyde To a solution of 2-bromo-5-trifluoromethyl benzonitrile (20.16 mmoles) in methylene chloride (50 ml), under argon at room temperature, was added diisobutyl-aluminum hydride (25 mmoles, 25 ml hexane) dropwise and the resulting solution was stirred for 30 minutes. The reaction mixture was diluted with ether (50 ml), cooled in ice and quenched by the careful addition of hydrochloric acid (50 ml, 3N). The ice bath was removed and the mixture was stirred vigorously for 15 minutes. The organic layer was washed with brine (50 ml), treated with magnesium sulfate-charcoal and evaporated. The resulting oil was purified by distillation to give 2-bromo-5-trifluoromethyl benzaldehyde, bp 50°–55° C. at 0.05 mm Hg. A mixture of this compound (16.24 mmoles), 1-phenylocta-1,7-diyne (19.54 mmoles, prepared as in Example 7b), cuprous iodide (0.19 mmole) and bis(triphenylphosphine) palladium (II)

chloride (0.34 mmole) in triethylamine (50 ml) was refluxed under argon for 30 minutes. The reaction mixture was cooled and filtered. The filtrate was evaporated, taken up in ether (100 ml), washed with hydrochloric acid (50 ml, 3N) and sodium chloride, and treated with magnesium sulfate-charcoal. Filtration and evaporation left an oil which was purified by flash chromatography (5% ether/hexane) to yield 2-(8-phenyloctadiyn-1,7-yl)-5-trifluoromethyl benzaldehyde as an oil. A solution of this compound (13.26 mmoles) in ethyl acetate (100 ml) was treated with charcoal for 30 minutes and then filtered. The solution was then shaken under 50 psi of hydrogen with 10% palladium on charcoal (502 mg) for about 90 minutes. Thin layer chromatography of the reaction mixture indicated about 50% reduction of the aldehyde to the alcohol. To re-oxidize the alcohol, the palladium catalyst was filtered off and manganese dioxide (20 g) was added. This mixture was then stirred at room temperature under argon for 18 hours. Filtration and evaporation gave an oil which was purified by flash chromatography (2% ether/hexane) to afford the product as an oil.

(b) t-Butyl 3-[2-(8-phenyloctyl)-5-trifluoromethylphenyl]-3-hydroxypropanoate

Following the procedure of Example 13(a), the compound of Example 14(a) (5.1 mmoles) was converted to the named product.

(c) t-Butyl 3-[2-(8-phenyloctyl)-5-trifluoromethylphenyl]-3-methanesulfonyloxypropanoate The compound of Example 14(b) (2.0 mmoles) was dissolved in methylene chloride (10 ml) under argon and the solution cooled to −10° C. Triethylamine (6.6 mmoles) was added and the methanesulfonyl chloride (2.2 mmoles) in methylene chloride (3 ml) was added dropwise. The mixture was stirred in the cold for 30 minutes and poured into ice/water/methylene chloride. The separated organic layer was washed with cold ammonium chloride solution, water and brine, and then dried and concentrated to give the product as an oil.

(d) t-Butyl 3-[2-(8-phenyloctyl)-5-trifluoromethylphenyl]propenoate

The compound of Example 14(c) (1.97 mmoles) was dissolved in methylene chloride (10 ml) under argon and the solution cooled to 0° C. Triethylamine (6.3 mmoles) in methylene chloride (5 ml) was added dropwise and the mixture allowed to warm to room temperature for 18 hours and poured into ice/water/methylene chloride. The separated organic layer was washed with cold ammonium chloride solution, water and brine, and then dried and concentrated to give the product as an oil.

Alternatively, the compound of Example 14(a) is reacted with t-butyl (triphenylphosphoranylidene)acetate to give the product of Example 14(d).

(e) t-Butyl 3-(2-carboxyethylthio)-[2-(8-phenyloctyl)-5-trilfuoromethylphenyl]propanoate Following the procedure of Example 10(b) the compound of Example 14(d) (1.86 mmoles) was converted to the named product.

(f) 3-(2-Carboxyethylthio)-3-[2-(8-phenyloctyl)-5-trifluoromethylphenyl]propanoic acid Following the procedure of Example 10(c) the compound of Example 14(e) (1.65 mmoles) was hydrolyzed with trifluoroacetic acid (6 ml) and then worked up as described in Example 13(b) to afford the desired product as an oil. The oil (1.16 mmoles) is similarly treated with aqueous potassium carbonate (2.9 mmoles) to give after lyophilization the dipotassium salt.

Analysis for $C_{27}H_{31}F_3O_4S.K_2\frac{1}{2}H_2O$: Calculated: C, 54.84; H, 5.37. Found: C, 55.06; H, 5.79.

EXAMPLE 15

Preparation of 5-(2-Carboxyethylthio)-5-(2-dodecylphenyl)-4-hydroxypentanoic acid (a) 2-Dodecylbromobenzene To a solution of 1-bromoundecane (0.34 mole) in acetonitrile (800 ml) was added triphenylphosphine (0.37 mole), under argon, and the mixture was refluxed for 24 hours. The reaction mixture was allowed to cool to room temperature and the solvent was removed in vacuo. The resulting oil was redissolved in acetonitrile (100 ml) and then ether (1.2 l) was added. The ether was decanted and the procedure was repeated 4 times, at which point a solid came out of the ether. The solid was collected, washed with ether and air-dried to give the phosphonium salt. The latter (16.2 mmoles) was dissolved in tetrahydrofuran (66 ml), under argon, cooled to 0° C. and n-butyl lithium (7.4 ml, 2.2M in hexane, 16.2 mmoles) was added dropwise over a 10 minute period. This solution was stirred at 0° C. for 15 minutes and then a solution of 2-bromobenzaldehyde (13.5 mmoles) in tetrahydrofuran (15 ml) was added dropwise over 10 minutes. The reaction mixture was stirred for 15 minutes and then the solvent was removed in vacuo. Ether was added to the residue and allowed to sit for 18 hours. The ether layer was filtered away from the gummy residue and the residue treated 3 more times with ether. The combined ether extract was concentrated and flash chromatographed on silica, eluted with hexane, to give a mixture of cis and trans 2-(1-dodecenyl)bromobenzene. The mixture (5.57 mmoles) was dissolved in toluene (75 ml) and ethanol (75 ml) and then tris(triphenylphosphine) rhodium chloride catalyst (0.7 g) was added. The suspension was degassed with argon for 30 minutes and purged with hydrogen under argon for 1 hour. The mixture was hydrogenated at 50 psi for 6 hours and then left standing under hydrogen pressure for 60 hours. The reaction mixture was shaken for 2 hours, argon was bubbled in and the solid filtered. The filtrate was concentrated, the residue triturated with ether and then filtered. This filtrate was treated with charcoal, silica and filtered. The filtrate was concentrated, the residue redissolved in hexane and treated with silica. Concentration of the filtrate gave the product as a solid.

(b) 1-(2-Dodecylphenyl)-1-hydroxy-2-propene

The compound of Example 15(a) (6.15 mmoles) dissolved in tetrahydrofuran (5 ml) was added dropwise to magnesium turnings (5.63 mmoles) and tetrahydrofuran (2 ml), under argon, and the mixture refluxed for 1.5 hours. The reaction mixture was cooled and freshly distilled acrolein (5.12 mmoles) in tetrahydrofuran (5 ml) was added dropwise. The mixture was refluxed for 2 hours, cooled and ice-cold 10% hydrochloric acid was added. After stirring for another hour, the layers were separated and the aqueous layer extracted once. The combined extract was dried, concentrated and the crude product flash chromatographed on silica, eluted with 10% ethyl acetate/hexane, to give the product.

(c) Ethyl 5-(2-Dodecylphenyl)-E-4-pentenoate

The compound of Example 15(b) (2.7 mmoles) was dissolved in triethylorthoacetate (18.9 mmoles) and propionic acid (0.16 mmole) was added. The mixture was flushed with argon and heated in an oil bath (140° C.) for 1 to 1.5 hours, the ethanol produced in the reaction being distilled off. The reaction mixture was concentrated and the residue flash chromatographed on silica, eluted with 4% ethyl acetate/hexane, to give the product.

(d) Ethyl 5-(2-Dodecylphenyl)-E-4,5-epoxypentanoate

The compound of Example 15(c) (1.28 mmoles) was dissolved in methylene chloride, cooled to 10° C. under argon, and meta-chloroperbenzoic acid (1.50 mmoles) in methylene chloride (7 ml) was added dropwise, with stirring. The mixture was stirred at room temperature for 18 hours. Diethyl ether was added to the reaction mixture and the organic layer was washed with 5% sodium bicarbonate solution and saturated sodium chloride solution. The dried organic extract (over sodium sulfate) was concentrated in vacuo to give the crude product which was flash chromatographed on silica, eluted with 2% ethyl acetate/hexane, to give the product.

(e) Ethyl 5-(2-Dodecylphenyl)-5-(2-carbomethoxyethylthio)-4-hydroxypentanoate and its lactone To a solution of the compound of Example 15(d) (0.695 mmole) in methanol (10 ml) was added methyl 3-mercaptopropionate (2.0 mmoles). After 15 minutes, a solution of triethylamine (2.75 mmoles) in methanol was added dropwise and the mixture was stirred in the dark, under argon, for 60 hours. The reaction mixture was concentrated in vacuo and azeotroped with methylene chloride. The crude product was flash chromatographed on silica, eluted first with 8% ethyl acetate/hexane and then with 15% ethyl acetate/hexane to give a 2:1 mixture of lactone and straight chain product.

(f) 5-(2-Carboxyethylthio)-5-(2-dodecylphenyl)-4-hydroxypentanoic acid

The mixture obtained in Example 15(e) (0.6 mmole) was dissolved in methanol (4 ml) and sodium hydroxide (3.0 mmoles) in water (1 ml) was added. The mixture was stirred at room temperature for 18 hours, concentrated and the pH adjusted to 4 with phosphoric acid. The product was extracted into ether, and the dried extract was concentrated. The residual oil was taken up in ether, washed with water, saturated sodium chloride solution and then dried over sodium sulfate. The organic layer was concentrated in vacuo to leave the desired product as an oil, $-\log K_B$ value 6.2 (active once, inactive twice, average value 2.07).

Analysis for $C_{26}H_{42}O_5S$: Calculated: C, 69.29; H, 9.39. Found: C, 69.25; H, 9.00.

EXAMPLE 16

Preparation of 5-(2-Dodecylphenyl)-4-hydroxy-5-(1-methyl-5-carboxy-2-imidazolylthio)pentanoic acid (a) Ethyl 5-(2-Dodecylphenyl)-5-(1-methyl-5-carbomethoxy-2-imidazolylthio)-4-hydroxypentanoate and its lactone A solution of 1-methyl-5-carbomethoxy-2-thioimidazole (1.71 mmoles) in triethylamine (0.32 ml) and methanol (25 ml) was added dropwise with stirring to the compound of Example 15(d) (0.9 mmole), under argon at room temperature. The mixture was stirred for 60 hours, concentrated in vacuo and azeotroped with methylene chloride. The crude product was flash chromatographed on silica, eluted with 10% ethyl acetate/hexane, progressing to 25% ethyl acetate/hexane to give a mixture of lactone and straight chain product.

(b) 5-(2-Dodecylphenyl)-4-hydroxy-5-(1-methyl-5-carboxy-2-imidazolylthio)pentanoic acid The mixture of Example 16(a) (0.7 mmole) was dissolved in methanol (8 ml) and a solution of sodium hydroxide (0.143 g in 1.5 ml water) was added dropwise with stirring. The mixture was stirred at room temperature for 18 hours and then concentrated in vacuo. The pH was adjusted to 4 with 10% phosphoric acid and the product extracted into ether/ethyl acetate. The organic extract was washed with water, saturated sodium chloride solution and then dried over sodium sulfate. The organics were removed in vacuo and the residue azeotroped with ether to give the desired product as a solid, mp 79°-80° C., $-\log K_B$ value 5.9.

Analysis for $C_{28}H_{42}N_2O_5S \cdot \frac{1}{2}H_2O$: Calculated: C, 63.73; H, 8.21; N, 5.31. Found: C, 63.68; H, 7.95; N, 5.30

EXAMPLE 17

Preparation of 5-(2-Carboxyethylthio)-5-(2-dodecylphenyl)pentanoic acid (a) 6-(2-Dodecylphenyl)-tetrahydro-4-H-pyran-2-one To the Grignard reagent generated from the compound of Example 15(a) (6.15 mmoles) and magnesium (5.7 mmoles) in tetrahydrofuran, cooled to −78° C., was added chloro titanium triisopropoxide (5.6 mmoles) in hexane, dropwise (the titanium reagent was prepared from titanium tetra-isopropoxide and titanium tetrachloride). The reaction mixture was allowed to warm slowly to room temperature and the titanium intermediate was stirred for 10 minutes at this temperature. The mixture was then cooled to −15° C. and methyl 5-oxovalerate (5.1 mmoles) in tetrahydrofuran was added dropwise. The reaction mixture was stirred at room temperature for 2 hours and then quenched with ice/10% hydrochloric acid. Ether was added and the organic layer was washed with water and saturated sodium chloride solution. The dried organic extract was concentrated and the crude product was flash chromatographed on silica, eluted with 10% ethyl acetate/hexane, followed by 1% acetone/methylene chloride or methylene chloride alone, to separate the lactone product.

(b) 5-(2-Carboxyethylthio)-5-(2-dodecylphenyl)pentanoic acid

A mixture of the compound of Example 17(a) (0.5 mmole), 3-mercaptopropionic acid (0.5 ml) and zinc iodide (0.5 mmole) in 1,2-dichloroethane (15 ml) was stirred at room temperature for 3 days. The reaction mixture was quenched with ice-water and diluted with carbon tetrachloride (85 ml). The separated organic layer was washed with carbon tetrachloride, dried over magnesium sulfate and evaporated to give the desired product as an oil, $-\log K_B$ value 5.5.

Analysis for $C_{26}H_{42}O_4S$: Calculated: C, 69.29; H, 9.39. Found: C, 69.06; H, 9.29.

EXAMPLE 18

Preparation of 5-(2-Dodecylphenyl)-5-(1-methyl-5-carboxy-2-imidazolylthio)pentanoic acid A mixture of the compound of Example 17(a) (0.51 mmole) and 1-methyl-5-carbomethoxy-2-thioimidazole (0.55 mmole) in trifluoroacetic acid (15 ml) was stirred at room temperature for 18 hours. The reaction mixture was evaporated and the residue was partitioned between methylene chloride and ice water. The aqueous layer was separated and extracted with methylene chloride. The combined extract was dried over magnesium sulfate and evaporated to give 5-(2-dodecylphenyl)-5-(1-methyl-5-carbomethoxy-2-imidazolylthio)pentanoic acid. This methyl ester intermediate, after purification by flash column chromatography on silica with 30% ethyl acetate in hexane and 0.4% formic acid, was hydrolyzed with 10% sodium hydroxide (2 ml) and 40% sodium hydroxide (5 drops) in methanol (15 ml) at room temperature for 18 hours. The mixture was acidified with 3N hydrochloric acid, extracted with methylene chloride, dried over magnesium sulfate and evaporated to give the desired product as an oil, $-\log K_B$ value 5.2.

Analysis for $C_{28}H_{42}N_2O_4S \cdot \frac{1}{2}H_2O$: Calculated: C, 65.72; H, 8.47; N, 5.47. Found: C, 65.62; H, 8.21; N, 4.92.

EXAMPLE 19

Preparation of 2-(Carboxymethylthio)-2-(2-undecyloxyphenyl)acetic acid (a) 2-undecyloxybenzaldehyde To a stirred suspension of sodium hydride (10.0 mmoles), which was prewashed with petroleum ether, in sieve dried dimethylformamide (10 ml) was added dropwise a solution of salicylaldehyde (10.1 mmoles) in dimethylformamide (1 ml). To the reaction mixture was then added undecyl bromide (10.0 mmoles) and the mixture stirred for 16 hours at ambient temperature under nitrogen. The reaction mixture was taken up in hexane (50 ml) and washed with 10 percent sodium hydroxide (2×50 ml) and saturated sodium chloride (50 ml). The organic phase was dried over anhydrous magnesium sulfate and charcoal. Evaporation of the volatiles yielded a colorless liquid which was purified by flash chromatography over silica gel with 2 percent ethyl acetate in hexane as eluant to afford the desired product as an oil.

Analysis for $C_{18}H_{28}O_2$: Calculated: C, 78.21; H, 10.21. Found: C, 77.92; H, 9.95.

(b) 2-(Carboxymethylthio)-2-(2-undecyloxyphenyl) acetic acid

Employing the general methods of Example 1(d)–1(f), the compound of Example 19(a) is converted to the desired product.

The following compounds are prepared according to the general methods described above from the appropriately substituted hydroxybenzaldehyde and the appropriate alkyl halide:

2-(Carboxymethylthio)-2-(2-nonyloxyphenyl) acetic acid;

2-(Carboxymethylthio)-2-(5-methoxy-2-undecyloxyphenyl) acetic acid;

2-(Carboxymethylthio)-2-(5-bromo-2-undecyloxyphenyl) acetic acid; and 2-(Carboxymethylthio)-2-(5-nitro-2-undecyloxyphenyl) acetic acid.

2-(Carboxymethylthio)-2-(2-undecylthiophenyl) acetic acid is prepared from 2-undecylthiobenzaldehyde.

EXAMPLE 20

Alternate Preparation of Alkoxybenzaldehyde Intermediates (a) 2-Undecyloxybenzaldehyde A mixture of salicylaldehyde (10.15 moles), undecylbromide (10.3 mmoles) and potassium carbonate (11.7 mmoles) in dimethylformamide (10 ml) is heated to 100° C. for 1 hour and then is cooled. The reaction mixture is taken up in hexane and is washed with 5 percent sodium hydroxide and brine. After treatment with anhydrous magnesium sulfate and charcoal, the volatiles are removed under vacuum and the residue is purified by flash chromatography to give the desired product.

EXAMPLE 21

Preparation of 3-(2-Carboxyethylthio)-3-[2-(1-dodecyn-1-yl)phenyl]-propanoic acid (a) 2-(1-Dodecyn-1-yl)benzaldehyde A mixture of 2-bromobenzaldehyde (10.05 mmoles), 1-dodecyne (12.03 mmoles), cuprous iodide (0.11 mmole) and bis(triphenylphosphine) palladium chloride (0.20 mmole) in freshly distilled triethylamine (30 ml.) was heated for one hour at reflux producing a white precipitate. The reaction mixture was cooled and filtered. The filtrate was evaporated to dryness at reduced pressure and then dissolved in diethyl ether (50 ml) and washed with brine (50 ml). After treatment with anhydrous magnesium sulfate and charcoal, the solution was evaporated to afford a dark oil, which was purified by flash chromatography (2% diethyl ether/hexane) to yield the desired product.

(b) 3-(2-Carboxyethylthio)-3-[2-(1-dodecyn-1-yl)phenyl]-propanoic acid

Employing the general methods of Example 13, the compound of Example 21(a) is converted to the desired product.

EXAMPLE 22

Preparation of
3-(2-Carboxyethylthio)-3-[2-(6-phenylhexyloxy)-
phenyl]propanoic acid (a) 2-(6-Phenylhexyloxy)benzaldehyde A solution of 6-phenylhexanoic acid (19.8 mmoles) in sieve dried tetrahydrofuran (5 ml) and reduced with diborane in tetrahydrofuran (30 ml, 29.1 mmoles) at 0° C. for 4 hours to give 6-phenylhexanol. To an ice cold solution of the hexanol (ca. 19.8 mmoles) and carbon tetrabromide (21.98 mmoles) in methylene chloride (50 ml) was added triphenylphospine (22.30 mmoles) in methylene chloride (50 ml) and the resulting solution was stirred for 2.5 hours. The volatiles were evaporated and the residue was taken up in ether (100 ml), cooled in ice, and filtered. The filtrate was evaporated and distilled to afford 6-phenylhexyl bromide as an oil. A mixture of the bromide (8.00 mmoles), salicylaldehyde (8.19 mmoles) and potassium carbonate (9.33 mmoles) in dimethylformamide (10 ml) was heated to 100° C. and maintained at that temperature for one hour. The cooled reaction mixture was taken up in hexane (50 ml) and washed with 5% sodium hydroxide (50 ml) and saturated sodium chloride (50 ml). The organic phase was dried over anhydrous magnesium sulfate and charcoal. Evaporation yielded a colorless oil which was purified by flash chromatography over silica gel with 5% ethyl acetate in hexane as eluant to afford the desired product as an oil.

Analysis for $C_{19}H_{22}O_2$: Calculated: C, 80.82; H, 7.85. Found: C, 80.62; H, 7.72.

(b)
3-(2-Carboxyethylthio)-3-[2-(6-phenylhexyloxy)-
phenyl]propanoic acid

Employing the general methods of Example 13, the compound of Example 22(a) is converted to the desired product.

EXAMPLE 23

Preparation of
3-(2-Carboxyethylthio)-3-[2-(12,12,12-tri-
fluorododecyl)phenyl]propanoic acid (a) 2-(12,12,12-Trifluorododecyl)benzaldehyde Following the procedures of Example 1(a), (b) and (c), 12,12,12-trifluorododecylmagnesium bromide (from 29.19 mmoles of 12,12,12-trifluorododecyl bromide and 25.71 mmoles of magnesium) was reacted with 2-(2-methoxyphenyl)-4,4-dimethyloxazoline (20.17 mmoles) in tetrahydrofuran to give 2-[2-(12,12,12-trifluorododecyl)phenyl]-4,4-dimethyloxazoline. The oxazoline (14.39 mmoles) was converted to the methiodide salt and then reduced with sodium borohydride (13.43 mmoles) to yield the desired product as an oil.

Analysis for $C_{19}H_{27}F_3O$: Calculated: C, 69.49; H, 8.29. Found: C, 69.14; H, 8.31.

(12,12,12-Trifluorododecyl bromide was obtained by reaction of 12-bromododecanoic acid with an excess of sulfur tetrafluoride under pressure at 125° C. for 10 hours.)

(b)
3-(2-Carboxyethylthio)-3-[2-(12,12,12-tri-
fluorododecyl)phenyl]propanoic acid Employing the general methods of Example 13, the compound of Example 23(a) is converted to the desired product.

EXAMPLE 24

Preparation of
3-(2-Carboxyethylthio)-3-[2-(8-cyclohexyloctyl)-
phenyl]propanoic acid (a) 2-(8-Cyclohexyloctyl)benzaldehyde To an ice cold solution of 1-hexyne (49.6 mmoles) in freshly distilled tetrahydrofuran (50 ml) containing a trace of triphenylmethane was added dropwise n-butyl lithium in hexane (49.5 mmoles). About 10 minutes after the addition was stopped, sieve dried hexamethylphosphoramide (57.5 mmoles) was added and the solution stirred for 10 minutes. A solution of 2-cyclohexylethyl bromide (51.3 mmoles) in tetrahydrofuran (10 ml) was added and the reaction mixture was stirred for about 3 hours as the temperature rose to room temperature. The mixture was taken up in ether (100 ml) and washed with water (3×100 ml) and sodium chloride solution (100 ml). The organic phase was dried over magnesium sulfate and evaporated to leave an oil which was purified by flash chromatography to give 1-cyclohexyloct-3-yne. This compound (20.8 mmoles) was treated with potassium hydride (36.8 mmoles) in propylene diamine to obtain the isomeric 8-cyclohexyloct-1-yne as an oil. A mixture of 2-bromobenzaldehyde (12.59 mmoles), 8-cyclohexyloct-1-yne (14.87 mmoles), cuprous iodide (0.17 mmoles) and bis(triphenylphosphine) palladium (II) chloride (0.26 mmoles) in triethylamine (35 ml) was refluxed under argon for 1.5 hours. The reaction mixture was cooled, filtered and the filtrate evaporated. The resulting residue was dissolved in ether (100 ml), washed with 3N hydrochloric acid (50 ml) and saturated sodium chloride solution (50 ml) and then dried over anhydrous magnesium sulfate and charcoal. The solution was evaporated to afford an oil which was purified by flash chromatography (2% ether/hexane) to yield 2-(8-cyclohexyl-1-octynyl)benzaldehyde as an oil. This benzaldehyde (10.22 mmoles) was hydrogenated with 10% palladium on charcoal in ethyl acetate to give the desired product as an oil, after chromatography (3% ether/hexane).

Analysis for $C_{21}H_{32}O$: Calculated: C, 83.94; H, 10.73. Found: C, 82.70, 82.53; H, 10.49, 10.68.

(b)
3-(2-Carboxyethylthio)-3-[2-(8-cyclohexyloctyl)-
phenyl]propanoic acid

Employing the general methods of Example 13, the compound of Example 24(a) is converted to the desired product.

EXAMPLE 25

Preparation of
3-(2-Carboxyethylthio)-3-[2-(11-dodecynyl)phenyl]-
propanoic acid (a) 2-(11-Dodecynyl)benzaldehyde To a solution of trimethylsilylacetylene (66.6 mmoles) in tetrahydrofuran (25 ml) cooled to −15° C., under argon, was added dropwise n-butyl lithium (25.6 ml, 2.6M in hexane). The resulting solution was stirred for 15 minutes and hexamethylphosphoramide (25 ml) was added. After stirring for 15 minutes the solution was cooled further to −78° C. and 1,10-decyl dibromide (66.6 mmoles) in tetrahydrofuran (150 ml) was added all at once. The reaction mixture was allowed to warm to room temperature and then poured into ice water/ether. The organic layer was washed with water and saturated sodium chloride solution, dried and concentrated. The residual product was purified by flash chromatography (silica column, eluted with hexane) to give 12-trimethylsilyl 11-dodecynyl bromide. This compound (26.15 mmoles) in tetrahydrofuran (50 ml) was added to magnesium turnings (22.35 mmoles) and to the resulting Grignard reagent was added 2-(2-methoxyphenyl)-4,4-dimethyloxazoline (14.9 mmoles) in tetrahydroduran (30 ml). The solution was stirred under argon at room temperature for 18 hours, cooled and aqueous ammonium chloride was added dropwise. The reaction mixture was diluted with water and ether, and the organic layer was dried and evaporated to leave the product which was purified by flash chromatography to give 2-(12-trimethylsilyl 11-dodecynylphenyl)-4,4-dimethyloxazoline. A solution of this compound (7.36 mmoles) in methyl iodide (25 ml) was refluxed for 15 hours. The volatiles were removed under vacuum to leave the semi-solid 2-(12-trimethylsilyl 11-dodecynylphenyl)-3,4,4-trimethyloxazolinium iodide. To a cooled solution (0° C.) of this compound (6.96 mmoles) in methanol (30 ml) was added in portions sodium borohydride (7.30 mmoles). The reaction mixture was stirred for 30 minutes and was then quenched with 5% sodium hydroxide solution. The product was extracted into ether and the dried extract was concentrated to leave an oil which was dissolved in acetone (50 ml). Hydrochloric acid (10 ml, 3N) was added and the mixture was stirred at room temperature for 18 hours. The acetone was removed in vacuo and the residue partitioned between water and ether. The organic layer was dried and concentrated to give the product which was purified by flash chromatography to give as an oil, 2-(12-trimethylsilyl 11-dodecynyl)benzaldehyde. This compound (2.86 mmoles) was dissolved in methanol (10 ml) under argon, and potassium carbonate (100 mg) was added. The mixture was stirred at room temperature for 18 hours and the solvent removed in vacuo. The residue was dissolved in methylene chloride and the solution washed with 5% sodium bicarbonate solution, water and brine. The dried solution was conentrated to give the desired 2-(11-dodecynyl)benzaldehyde as an oil.

(b) 3-(2-Carboxyethylthio)-3-[2-(11-dodecynyl)phenyl]-propanoic acid

Employing the general method of Example 13, the compound of Example 25(a) is converted to the desired product.

EXAMPLE 26

Preparation of 4-Thia-5-(2-dodecylphenyl)-5-(tetrazol-5-yl) pentanoic acid (a) 2-Dodecylbenzoic acid A solution containing lithium diisopropylamide (0.1 mole) was prepared by treating a solution of diisopropylamine (14.1 ml, 0.1 mole) in tetrahydrofuran (200 ml) at 0° C. with n-butyl lithium (41.2 ml of a 2.43M solution, 0.1 mole), and stirring for 5 minutes. To this was added a solution of o-toluic acid (6.8 g, 0.05 mole) in tetrahydrofuran (50 ml). The ice bath was removed and the intense red solution was stirred for 30 minutes. This solution was slowly pipetted into a solution of undecylbromide (11.8 g, 0.05 mole) in tetrahydrofuran (50 ml) at −20° C. After the addition, the cooling bath was removed and the solution stirred for 30 minutes. A small amount of water was added and most of the tetrahydrofuran was removed under reduced pressure. The residue was poured into water, acidified with 3N hydrochloric acid and extracted with ether. The ether was dried, evaporated and the residue was recrystallized from acetonitrile, then from hexane, to give the product.

(b) 2-Dodecylbenzyl alcohol

A solution of the compound of Example 26(a) (19.0 g, 66 mmoles) in ether (200 ml) was slowly added to a stirred slurry of lithium aluminum hydride (2.5 g, 66 mmoles), in ether (500 ml), at 0° C. The ice bath was removed and stirring continued 2 hours. Water (2.5 ml) was cautiously added, followed by 10% sodium hydroxide solution (3.75 ml) and water (6.25 ml). The solids were filtered, the filtrate was evaporated and the crude residue was recrystallized from acetonitrile to give the product.

(c) 2-Dodecylbenzyl nitrile

A solution of the compound of Example 26(b) (11.7 g, 42 mmoles) in a mixture of methylene chloride (300 ml) and pyridine (5.1 ml, 63 mmoles) at 0° C. was treated slowly with thionyl chloride (7.5 g, 63 mmoles). The ice bath was removed and stirring continued for 4 hours. The solvents were evaporated and the residue taken up in ether. The ether was washed with water, dried and evaporated to give crude 2-dodecylbenzyl chloride.

This crude chloride was dissolved in dimethylformamide (20 ml) and added to a cold (0° C.) suspension of potassium cyanide (4.13 g, 63 mmoles) in dimethylformamide (50 ml). The ice bath was removed and stirring was continued for 18 hours at 23° C. and 30 minutes at 95° C. The reaction mixture was poured onto ice and extracted with ether. The extract was washed with water, dried and evaporated. The residue was recrystallized from methanol to give the product.

(d) 5-(2-Dodecylbenzyl)tetrazole

A mixture of the compound of Example 26(c) (4.0 g, 14 mmoles), sodium azide (5.48 g, 84 mmoles) and ammonium chloride (4.5 g, 83 mmoles) in dimethylformamide (50 ml), under argon, was heated at 135° C. for 30 hours. The mixture was cooled, poured into water (100 ml), acidified with concentrated hydrochloric acid and extracted thoroughly with ether. The extracts were washed several times with water, dried and evaporated. The crude product was recrystallized from acetonitrile to give the product.

(e) Methyl 4-thia-5-(2-dodecylphenyl)-5-tetrazol-5-yl)pentanoate

A solution of diisopropylamine (0.85 ml, 6.1 mmoles) in tetrahydrofuran (10 ml) at 0° C. was treated with n-butyl lithium (6.1 mmoles). After 5 minutes a solution of the compound of Example 26(d) (1.0 g, 3.05 mmoles) in tetrahydrofuran (5 ml) was added. The deep yellow solution was stirred for 30 minutes and then cooled to −78° C. A solution of 2-carbomethoxyethyl-p-toluenethiosulfonate (0.84 g, 3.05 mmoles) in tetrahydrofuran (5 ml) was added. The solution was warmed to 23° C., stirred for 30 minutes and poured into water (100 ml). The mixture was acidified with 3N hydrochloric acid and extracted with ethyl acetate. The extract was washed with water and 1N hydrochloric acid, dried and evaporated. The crude product was chromatographed over silica gel, eluting with hexane: ethyl acetate, 7:3, to give the product.

The 2-carbomethoxyethyl-p-toluenethiosulfonate used as above was obtained by reaction of a solution of di-2-carbomethoxyethyl disulfide (6.66 g, 28 mmoles) in acetone (200 ml) with a solution of silver nitrate (4.76 g, 28 mmoles) in water (20 ml), followed by a solution of sodium p-toluenesulfinate (6.0 g, 28 mmoles) in warm water (60 ml). After stirring for 1 hour, the reaction mixture was filtered. The filtrate was concentrated and extracted with ethyl acetate. The extract was washed with water, dried and evaporated to give the desired thiosulfonate.

(f) 4-Thia-5-(2-dodecylphenyl)-5-(tetrazol-5-yl)pentanoic acid

A solution of the ester prepared in Example 26(e) (120 mg, 0.27 mmole) in methanol (3 ml) was diluted with water (6 ml). To the resulting suspension was added 10% sodium hydroxide solution (0.5 ml) and the clear solution was stirred at 23° C. for 11 hours. Water (5 ml) was added, the solution was acidified with 3N hydrochloric acid and extracted with ethyl acetate. The extract was dried and evaporated. The crude product was chromatographed over silica gel and eluted with ethyl acetate:hexane:acetic acid, 50:50:0.5, to give the product. The structure was confirmed by nuclear magnetic resonance and mass spectra data.

EXAMPLE 27

Preparation of 4-Thia-5-(2-dodecylphenyl)-5-carboxamidopentanoic acid (a) 2-(2-Dodecylphenyl)acetic acid A solution of the compound of Example 26(c) (5.4 g, 19 mmoles) and sodium hydroxide (4.0 g, 0.1 mole) in water (20 ml) and ethanol (60 ml) was refluxed for 8 hours. Water (100 ml) was added and the mixture was filtered. The filtrate was acidified with 3N hydrochloric acid and the resulting solid was extracted into ethyl acetate. The extract was dried and evaporated to give the product.

(b) 2-(2-Carbomethoxyethylthio)-2-(2-dodecylphenyl)acetic acid

A solution of diisopropylamine (4.6 ml, 33 mmoles) in tetrahydrofuran (40 ml) at −20° C. was treated with n-butyl lithium (36 mmoles). After 5 minutes the temperature was raised to 0° C. and a solution of the compound of Example 27(a) (5.0 g, 16.4 mmoles) in a mixture of tetrahydrofuran (10 ml) and hexamethylphosphoramide (5 ml) was added. After stirring for 1 hour, this solution was slowly added to a solution of 2-carbomethoxyethyl-p-toluenethiosulfonate (5.98 g, 16.4 mmoles) in tetrahydrofuran (30 ml) at −78° C. After 30 minutes, water (200 ml) was added to the cold reaction mixture. It was warmed to 23° C. acidified with 3N hydrochloric acid and extracted with ethyl acetate. The extracts were washed with water, 1N hydrochloric acid, dried and evaporated. The crude residue was chromatographed over silica gel, eluted with a mixture of hexane:ethyl acetate:acetic acid, 80:19.5:0.5, to give the product as an oil.

(c) 2-(2-Carbomethoxyethylthio)-2-(2-dodecylphenyl)acetyl chloride

A solution of the compound of Example 27(b) (500 mg, 1.18 mmoles) in methylene chloride (15 ml) was stirred under argon at room temperature, and oxalyl chloride (0.114 ml, 1.3 mmoles) was added followed by pyridine (0.01 ml, 0.12 mmole). The reaction mixture was stirred at room temperature for 30 minutes and the solvent was removed to give the product.

(d) Methyl 4-thia-5-(2-dodecylphenyl)-5-carboxamidopentaonate

To the compound of Example 27(c) (330 mg, 0.75 mmole), stirred in an ice bath under argon, was added concentrated ammonium hydroxide (2 ml) and the mixture stirred for 15 minutes. The reaction mixture was diluted with water, extracted with ethyl acetate dried over anhydrous sodium sulfate, filtered and evaporated to give the product.

(e) 4-Thia-5-(2-dodecylphenyl)-5-carboxamidopentanoic acid

The compound of Example 27(d) (256 mg, 0.61 mmole) was dissolved in methanol and stirred under argon at 0° C. A 1N solution of sodium hydroxide (1.8 ml, 1.8 mmoles) was added dropwise, the ice bath removed and the mixture stirred at room temperature for 18 hours. The methanol was evaporated and the residue was cooled in an ice bath, acidified with dilute hydrochloric acid, extracted with ethyl acetate, filtered and evaporated. The crude product was recrystallized from ethyl acetate/hexane to give the product, mp 99°–100.5° C., −log $K_B$ value 5.1.

Analysis for $C_{23}H_{37}NO_3S$: Calculated: C, 67.77; H, 9.15; N, 3.44. Found: C, 67.83; H, 9.17; N, 3.04.

EXAMPLE 28

Preparation of 2-(2-Dodecylphenyl)-5-sulfo-3-thiapentanoic acid (a) Methyl 2-(2-dodecylphenyl)-5-sulfo-3-thiapentanoate The compound of Example 1(e) (0.75 g, 2.13 mmoles) was dissolved in methylene chloride (5 ml) under argon and triethylamine (0.41 ml, 2.98 mmoles) was added, followed by sodium thioethylsulfonate (0.49 g, 2.98 mmoles). Dimethylformamide (7 ml) was added and the mixture stirred at room temperature for 72 hours. The reaction mixture was poured into ice cold 3N hydrochloric acid/ethyl acetate. The separated organic layer was washed with water, until neutral pH, and sodium chloride solution, dried and concentrated to give the product.

(b) 2-(2-Dodecylphenyl)-5-sulfo-3-thiapentanoic acid

The compound of Example 28(a) (0.37 g, 0.8 mmole) was dissolved in methanol (4 ml), and a solution of sodium hydroxide (0.128 g in 1.5 ml water) was added dropwise. The mixture was stirred at room temperature for 18 hours, the methanol was removed in vacuo and the aqueous residue was flash chromatographed, eluted with 50:50 acetonitrile/water. The acetonitrile was removed in vacuo and the water lyophilized away to leave a white solid which was the desired product as the disodium salt, hydrate; $-\log K_B$ value 5.8.

Analysis for $C_{22}H_{34}O_5S_2 \cdot Na_2 \cdot \frac{3}{4}H_2O$: Calculated: C, 52.62; H, 7.13. Found: C, 52.41; H, 7.09.

EXAMPLE 29

Preparation of 2-(2-Dodecylphenyl)-4-carboxy-3-thiahexanedioic acid (a) 5-Carbomethoxy-5-(2-dodecylphenyl)-3-carboxy-4-thiapentanoic acid The compound of Example 1(e) (0.99 g, 2.8 mmoles) was dissolved in dimethylformamide (10 ml), and triethylamine (2.2 ml, 15.8 mmoles) was added followed by 2-thiobutanedioic acid (0.59 g, 3.94 mmoles). After about 10 minutes, additional triethylamine (1 ml) and dimethylformamide (10 ml) were added and stirring was continued at room temperature for 12 hours, under argon. The reaction mixture was poured into ice cold 10% hydrochloric acid/ethyl acetate and the layers separated. The organic layer was washed with water and saturated sodium chloride solution, and then dried over magnesium sulfate to give after evaporation the product as a mixture of 2 stereoisomers.

(b) 2-(2-Dodecylphenyl)-4-carboxy-3-thiahexanedioic acid

The compound of Example 29(a) (1.3 g, 2.995 mmoles) was dissolved in methanol (15 ml) and a solution of sodium hydroxide (0.72 g in 3 ml water) was added dropwise with stirring. The mixture was stirred for 48 hours, warmed to 35° C. for 3 hours and then stirred for 24 hours. The methanol was removed in vacuo and the residue was dissolved in ethyl acetate/dilute hydrochloric acid. The organic layer was washed with water and sodium chloride solution, and then dried over magnesium sulfate to give after concentration a residual oil. The latter was flash chromatographed on a silica column, eluted with 15–25% ethyl acetate/hexane/0.5% formic acid, to give the product, mp 85°–89° C., $-\log K_B$ value 5.8.

Analysis for $C_{24}H_{36}O_6S$: Calculated: C, 63.69; H, 802. Found: C, 63.54; H, 8.02.

EXAMPLE 30

Preparation of 2-(2-Sulfonamidoethylthio)-2-(2-dodecylphenyl)acetic acid (a) Methyl 2-(2-chlorosulfonylethylthio)-2-(2-dodecylphenyl) acetate The compound of Example 28(a) (1 g, 2.18 mmoles) was dissolved in dimethylformamide (5 ml), and thionyl chloride (0.19 ml, 2.62 mmoles) in dimethylformamide (1 ml) was added dropwise. The mixture was maintained at 0° C. for 1 hour and then cooled at $-15°$ C. for 18 hours. The reaction mixture was warmed to 0° C., additional thionyl chloride (0.1 ml) was added and stirring was continued at 0° C. for 1 hour. The mixture was poured into ice water/ethyl acetate and the organic layer was washed with water and sodium chloride soluion, then dried and concentrated. The residue as flash chromatographed on a silica column, eluted with 1–2% ethyl acetate/hexane/0.5% formic acid, to give the product as an oil.

(b) Methyl 2-(2-sulfonamidoethylthio)-2-(2-dodecylphenyl) acetate

To the compound of Example 30(a) (0.29 g, 0.609 mmole), chilled in ice/methanol, was added ice cold ammonium hydroxide (3 ml). The mixture was stirred for 1 minute, diluted with ethyl acetate and then water was added. The organic layer was washed with water and sodium chloride solution, then dried over magnesium sulfate and concentrated to give an oil. The oil was flash chromatographed on a silica column, eluted with 25% ethyl acetate/hexane/0.5% formic acid, to give the product as an oil.

(c) 2-(2-Sulfonamidoethylthio)-2-(2-dodecylphenyl) acetic acid

The compound of Example 30(b) (154.5 mg, 0.3375 mmole) was dissolved in methanol (1 ml), cooled to 0° C., and aqueous sodium hydroxide (4.1 mg, 1.0125 mmole, in 4 ml water) was added dropwise. The mixture was maintained at 0° C. for 15 minutes and then stirred at room temperature for 72 hours. The methanol was removed in vacuo and the residue was taken up in dilute hydrochloric acid/ethyl acetate. The organic layer was washed with water and sodium chloride solution, dried over magnesium sulfate and concentrated. The residue was triturated with hexane to give the solid product, mp 56°–58° C., $-\log K_B$ value 5.1.

Analysis for $C_{22}H_{37}NO_4S_2$: Calculated: C, 59.56; H, 8.41; N, 3.16. Found: C, 59.66; H, 8.38; N, 3.02.

EXAMPLE 31

Preparation of 3-(S-Glutathionyl)-3-[2-(8-phenyloctyl)phenyl]-propanoic acid

3-[2-(8-Phenyloctyl)phenyl]-3-hydroxypropanoic acid (85 mg, 0.24 mmole, obtained from the compound of Example 13(a) by hydrolysis) was dissolved in methylene chloride (7 ml), under argon, and the solution was cooled to 0° C. Glutathione (88 mg, 0.288 mmole) was added, and then trifluoroacetic acid (14 ml) was added dropwise to the ice cold suspension. The mixture was stirred at 0° C. for 2 hours and concentrated at 0° C. in vacuo. The residue was redissolved in trifluoroacetic acid (10 ml) and stirred at room temperature for 18 hours. The acid was removed in vacuo and the residue was azeotroped with methylene chloride. The crude product was dissolved in 0.3M potassium carbonate solution (29 ml) and chromatographed on a reverse phase support, eluting with 30% acetonitrile/water. The acetonitrile was removed in vacuo and the water lyophilized away to leave a white solid which was the desired product as the tripotassium salt, hydrate; $-\log K_B$ value 5.4.

Analysis for $C_{33}H_{42}N_3O_8S \ K_3 \ 1.5 \ H_2O$: Calculated: C, 50.49,; H, 5.78; N, 5.35. Found: C, 50.40; H, 5.92; N, 5.27.

EXAMPLE 32

Preparation of
3-(2-Carboxyethylthio)-3-(2-dodecylphenyl)-2-hydroxypropanic acid and
3-(2-Carboxyethylthio)-3-(2-dodecylphenyl)-2-hydroxypropionamide

(a) Ethyl 3-(2-dodecylphenyl)propenoate

The compound of Example 1(c) (3.3 g, 12 mmoles) and (carbethoxymethylene)triphenylphosphorane (4.6 g, 13.2 mmoles) were dissolved in toluene (50 ml), stirred under argon and heated to reflux for 75 minutes. The solvent was stripped and the residue flash chromatographed on 200 grams of silica gel eluted with 4% ethyl acetate/hexane to give the product as a clear colorless oil.

(b) 3-(2-Dodecylphenyl)prop-2-en-1-ol

The compound of Example 32(a) (4.0 g, 11.6 mmoles) was dissolved in toluene (50 ml) and stirred under argon. A solution of diisobutylaluminum hydride (16.7 ml of a 1.5M solution in toluene, 25 mmoles) was added dropwise over 15 minutes. The maximum temperature was 41° C. After an additional 15 minutes of stirring, the reaction mixture was worked up by careful dropwise addition of methanol (2.9 ml, 70 mmoles) followed by water (1.35 ml, 75 mmoles). After the addition was complete, ethyl acetate (100 ml) was added and the mixture stirred for 15 minutes during which time a precipitate formed. Filtration and evaporation of the filtrate gave the crude product which was flash chromatographed on 200 grams of silica gel, eluted with 15% ethyl acetate/hexane, to give the product.

(c) 3-(2-Dodecylphenyl)-2,3-epoxypropan-1-ol

The compound of Example 32(b) (3.3 g, 10.9 mmoles) was dissolved in methylene chloride (100 ml) and stirred under argon at room temperature. A 0.5N aqueous solution of sodium bicarbonate (30 ml) was added, followed by m-chloroperbenzoic acid (85%) 2.21 g, 10.9 mmoles) added in portions over a period of 45 minutes. After stirring for an additional 30 minutes, the phases were separated and the aqueous layer extracted with methylene chloride. The combined organic phases were dried over anhydrous sodium sulfate, filtered and evaporated. The residue was flash chromatographed on 200 grams of silica gel, eluted with 15% ethyl acetate/hexane, to give the product as a clear colorless oil.

(d) 3-(2-Carbomethoxyethylthio)-3-(2-dodecylphenyl)propan-1,2-diol

The compound of Example 32(c) (2.94 g, 9.24 mmoles) was dissolved in methanol (15 ml) containing 2% triethylamine and stirred under argon at room temperature. Methyl mercaptopropionate (1.72 ml, 15.2 mmoles) and triethylamine (3.83 ml, 27.5 mmoles) were dissolved in methanol (15 ml) and added dropwise to the above solution over a period of 10 minutes. The mixture was stirred for 18 hours at room temperature after which time the solvents were stripped and the residue flash chromatographed on silica gel eluted with 20% ethyl acetate/hexane to give the product.

(e) 2-(2-Carbomethoxyethylthio)-2-(2-dodecylphenyl)acetaldehyde

The compound of Example 32(d) (3 g, 6.84 mmoles) was dissolved in diethyl ether (13 ml) and stirred at room temperature in a water bath. A saturated solution (138 ml) of periodic acid in diethyl ether was added in a single portion and the mixture stirred for 2 minutes. The reaction mixture was immediately flash chromatographed on 250 grams of silica gel, eluted with 8% ethyl acetate/hexane, to give the product.

(f) Methyl 3-(2-Carbomethoxyethylthio)-3-(2-dodecylphenyl)-2-hydroxypropionate and 3-(2-Carbomethoxyethylthio)-3-(2-dodecylphenyl)-2-hydroxypropionamide The compound of Example 32(e) (2.5 g, 6.16 mmoles) was dissolved in methylene chloride (25 ml) and stirred at 0° C. under argon. Zinc iodide (200 mg, 0.63 mmole) was added followed by trimethylsilyl cyanide (0.89 ml, 6.45 mmoles). The ice bath was removed and the mixture stirred at room temperature for 1 hour. The solvents were stripped and methanol (25 ml) was added. The mixture was again cooled in an ice bath and excess hydrogen chloride was bubbled into the solution. The ice bath was removed and the mixture stirred at room temperature for 18 hours. Water was added and the mixture stirred for 2 hours. The solvents were stripped and the residue flash chromatographed on silica gel eluted with 15-50% ethyl acetate/hexane to give: erythro-methyl 3-(2-carbomethoxyethylthio)-3-(2-dodecylphenyl)-2-hydroxypropionate; threo-methyl 3-(2-carbomethoxyethylthio)-3-(2-dodecylphenyl)-2-hydroxypropionate; erythro-3-(2-carbomethoxyethylthio)-3-(2-dodecylphenyl)-2-hydroxypropionamide; and threo-3-(2-carbomethoxyethylthio)-3-(2-docecylphenyl)-2-hydroxypropionamide.

(g) Threo-3-(2-carboxyethylthio)-3-(2-dodecylphenyl)-2-hydroxypropanoic acid The threo propionate of Example 32(f) (550 mg, 1.18 mmoles) was dissolved in methanol (15 ml) and stirred under argon at 0° C. A 1N solution of sodium hydroxide (4.5 ml, 4.5 mmoles) was added dropwise. The ice bath was removed and the mixture stirred for 8 hours. The solvent was stripped and the aqueous residue was acidified with dilute hydrochloric acid at 0° C. Extraction with ethyl acetate followed by drying over anhydrous sodium sulfate, filtration and evaporation gave the crude product. Recrystallization from ethyl acetate/hexane gave the pure product, mp 73.5°-75° C., −log $K_B$ value 6.1.

Analysis for $C_{24}H_{38}O_5S$: Calculated: C, 65.72; H, 8.73. Found: C, 65.33; H, 8.68.

(h) Erythro-3-(2-carboxyethylthio)-3-(2-dodecylphenyl)-2-hydroxypropanoic acid The erythro propionate of Example 32(f) (205 mg, 0.44 mmole) was dissolved in methanol (7 ml) and stirred under argon in an ice bath. A 1N solution of sodium hydroxide (1.75 ml, 1.75 mmoles) was added dropwise, the ice bath removed and the mixture stirred for 18 hours. The methanol was stripped, the residue cooled in an ice bath, acidified with dilute hydrochloric acid, extracted with ethyl acetate, dried over anhydrous sodium sulfate, filtered and evaporated. The crude product was recrystallized from ethyl acetate/hexane to give the pure product, mp 67.5°-69° C.

Analysis for $C_{24}H_{38}O_5S$: Calculated: C, 65.72; H, 8.73. Found: C, 65.71; H, 8.83.

(i) Threo-3-(2-carboxyethylthio-3-(2-dodecylphenyl)-2-hydroxypropionamide

The threo propionamide of Example 32(f) (230 mg, 0.51 mmole) was dissolved in methanol (5 ml) and stirred under argon in an ice bath. A 1N solution of sodium hydroxide (0.6 ml, 0.6 mmole) was added dropwise, the ice bath removed and the mixture stirred at room temperature for 18 hours. The methanol was stripped, the residue acidified with dilute hydrochloric acid at 0° C., extracted with ethyl acetate, dried over anhydrous sodium sulfate, filtered and evaporated to give the crude product which was recrystallized from ethyl acetate/hexane to give the product, mp 97.5°-102° C., $-\log K_B$ value 5.3.

Analysis for $C_{24}H_{39}NO_4S$: Calculated: C, 65.87; H, 8.98; N, 3.20. Found: C, 65.55; H, 8.66; N, 3.11.

(j) Erythro-3-(2-carboxyethylthio)-3-(2-dodecylphenyl)-2-hydroxypropionamide

The erythro propionamide of Example 32(f) (210 mg, 0.47 mmole) was dissolved in methanol (5 ml) and stirred under argon in an ice bath. A 1N solution of sodium hydroxide (0.6 ml, 0.6 mmole) was added dropwise, the ice bath removed and the mixture stirred at room temperature for 18 hours. The methanol was stripped, the residue cooled in an ice bath, acidified with dilute hydrochloric acid, extracted with ethyl acetate, dried over anhydrous sodium sulfate, filtered and evaporated to give the crude product. Recrystallization from ethyl acetate/hexane gave the product, mp 99°-100.5° C., $-\log K_B$ value 5.5

Analysis for $C_{24}H_{39}NO_4S$: Calculated: C, 65.87; H, 8.98; N, 3.20. Found: C, 66.01; H, 9.02; N, 3.25. In this example erythro=2S,3R and 2R,3S racemate, and threo=2R,3R and 2R,3S racemate.

EXAMPLE 33

Preparation of 4-Thia-5-(2-dodecylphenyl)-6-(tetrazol-5-yl)hexanoic acid (a) Ethyl 2-(tetrazol-5-yl)-2-(2-dodecylbenzoyl)acetate A solution of i-propylcyclohexylamine (4.6 ml, 28 mmoles) in tetrahydrofuran (25 ml) at −20° C. was treated with a 2.12M solution of n-butyl lithium in hexane (13.2 ml, 28 mmoles). After stirring for 30 minutes, the solution was cooled to −78° C. and a solution of ethyl 2-(tetrazol-5-yl)acetate (2.17 g, 14 mmoles) in tetrahydrofuran (5 ml) and hexamethylphosphoramide (5 ml) was added. The temperature was raised to −20° C. and the solution stirred for 1 hour.

2-dodecylbenzoyl chloride was prepared from 2-dodecylbenzoic acid (4.06 g, 14 mmoles) and excess thionyl chloride in methylene chloride at 23° C. for 1 hour. Following evaporation of the solvents, the acid chloride was used without purification. A solution of this acid chloride in tetrahydrofuran (15 ml) was added to the cold solution of dianion prepared above, followed by an additional amount of 2.12M n-butyl lithium (6.6 ml). The solution was warmed to −20° C., stirred for 1 hour and poured into cold 1N hydrochloric acid. The mixture was extracted with diethyl ether. The extracts were washed with water, dried and evaporated. The crude product was recrystallized from acetonitrile.

(b) α-(Tetrazol-5-yl)-2-dodecylacetophenone

A solution of the compound of Example 33(a) (3.5 g, 8.2 mmoles) in acetic acid (12 ml) and concentrated hydrochloric acid (12 ml) was refluxed for 4 hours. After cooling and dilution with water (50 ml), the solid was filtered and washed with water. The solid was dissolved in chloroform, washed with water, dried and evaporated to give the product.

(c) α-(5-Tetrazolylmethyl)-2-dodecylbenzyl alcohol

A solution of the compound of Example 33(b) (2.24 g, 6.3 mmoles) in ethanol (20 ml) was treated with excess sodium borohydride and stirred at 23° C. for 4 hours. The reaction mixture was poured into water, acidified and extracted with a mixture of ether and ethyl acetate. The extracts were washed with water, dried and evaporated. The residue was chromatographed over silica gel. Elution with chloroform washed off impurities, then elution with a mixture of ethyl actetate in chloroform, 4:6, gave the product.

(d) Methyl 4-Thia-5-(2-dodecylphenyl)-6-(tetrazol-5-yl)hexanoate

A solution of the compound of Example 33(c) (0.3 g, 0.84 mmole) in trifluoroacetic acid (5 ml) and methyl mercaptopropionate (0.5 ml) was heated at 70° C. for 20 minutes, and then thoroughly evaporated. The residue was chromatographed over silica gel, eluting first with chloroform to remove impurities. Elution with a mixture of ethyl acetate and chloroform, 1:1, gave the product.

(e) 4-Thia-5-(2-dodecylphenyl)-6-(tetrazol-5yl)hexanoic acid

A stirred mixture of the compound of Example 33(d) (200 mg, 0.44 mmole) in methanol (5 ml) and water (10 ml) was treated with 10% sodium hydroxide solution (1.5 ml) was heated to 55° C. for 9.5 minutes. The solution was cooled, acidified and extracted with ethyl acetate. The extracts were dried, evaporated and the residue chromatographed over silica gel, eluted with a mixture of ethyl acetate and hexane, 3:1, to give the product. The structure was confirmed by nuclear magnetic resonance and mass spectra data.

EXAMPLE 34

Preparation of 2-(2-Cyanoethylthio)-2-(2-dodecylphenyl)acetic acid (a) Methyl 2-(2-cyanoethylthio)-2-(2-dodecylphenyl)acetate To a solution of the compound of Example 1(e) (704 mg, 2 mmoles) and 3-mercaptopropionitrile (232 mg, 2.66 mmoles) in methylene chloride (5 ml) was added triethylamine (3 mmoles) and the mixture was stirred at room temperature for 48 hours. The reaction mixture was washed with water, 5% potassium carbonate solution, water, dried, filtered and concentrated to give the product as an oil.

(b) 2-(2-Cyanoethylthio)-2-(2-dodecylphenyl)acetic acid

A solution of the compound of Example 34(a) (0.3 g, 0.81 mmole) in methanol (5 ml) and aqueous potassium carbonate (5 ml, 3M) was stirred at room temperature for 18 hours. The reaction mixture was concentrated in vacuo and redissolved in water. The aqueous solution was extracted with ethyl acetate, acidified, extracted with ethyl acetate, washed, dried and concentrated to give the product, $-\log K_B$ value 5.4.

Analysis for $C_{23}H_{35}NO_2S$: Calculated: C, 70.90; H, 9.05; N, 3.59. Found: C, 70.15; H, 9.08; N, 3.90.

EXAMPLE 35

Preparation of 3-(2-Carboxyethylthio)-3-[2-(8-phenyloctyl)phenyl]-2-hydroxypropanoic acid

(a) Methyl 3-[2-(8-Phenyloctyl)phenyl]-2,3-epoxypropionate

The compound of Example 7(a) (2.94 g, 10 mmoles) was dissolved in diethyl ether (25 ml) and the solution was stirred under argon at 0° C. Methyl chloroacetate (1.32 ml, 15 mmoles) was added, followed by the addition of sodium methoxide (810 mg, 15 mmoles). The mixture was stirred for 2.5 hours at ice bath temperature. A small quantity of water was added, the ether phase separated, dried over anhydrous sodium sulfate, filtered and evaporated. The residue was flash chromatographed on 80 grams of silica gel eluted with 5-30% ethyl acetate/hexane to give the product.

(b) Methyl 3-(2-Carbomethoxyethylthio)-3-[2-(8-phenyloctyl)phenyl]-2-hydroxypropionate The compound of Example 35(a) (1.2 g, 3.28 mmoles) was dissolved in methanol (20 ml) containing 2% triethylamine and stirred under argon at room temperature. Methyl 3-mercaptopropionate (0.623 ml, 5.45 mmoles) and triethylamine (1.45 ml, 9.84 mmoles) were dissolved in methanol (15 ml) and added dropwise. The mixture was stirred for 18 hours. The solvent was stripped and the residue eluted with 20% ethyl acetate/hexane to give a mixture of the desired product and its regioisomer, methyl 2-(2-carbomethoxyethylthio)-3-[2-(8-phenyloctyl)phenyl]-3-hydroxypropionate. The mixture was rechromatographed on 100 grams of neutral alumina to separate the desired product.

(c) Erythro-3-(2-carboxyethylthio)-3-[2-(8-phenyloctyl)phenyl]-2-hydroxypropanoic acid The desired product of Example 35(b) (320 mg, 0.66 mmole) was dissolved in methanol (10 ml) and stirred under argon at ice bath temperature. A 1N solution of sodium hydroxide (2.5 ml, 2.5 mmoles) was added dropwise, the ice bath removed, the mixture stirred at room temperature for 2.5 hours, and then cooled for 18 hours. After an additional 1 hour of stirring at room temperature, the methanol was stripped, the residue diluted with water and the pH adjusted to 3.5 with dilute hydrochloric acid. Extraction with ethyl acetate followed by drying over anhydrous sodium sulfate, filtration and evaporation gave the crude product which was flash chromatographed on 20 grams of silica gel eluted with 30:70:0.5 ethyl acetate:hexane:formic acid to give the free acid product.

This acid (230 mg, 0.5 mmole), under argon, was treated with a solution of potassium carbonate (276 mg, 2.0 mmoles) in water (5 ml), while stirring in an ice bath. The mixture was stirred for 10 minutes at 0° C. and then desalted on a $C_{18}$ column using about 6 column volumes of water to remove salt and excess potassium carbonate. The product was then eluted with 1:1 acetonitrile:water, the solvents evaporated and the aqueous residue lyophilized to give the dipotassium salt, hydrate.

Analysis for $C_{26}H_{34}O_5S$ 2K $H_2O$: Calculated: C, 56.49; H, 6.20; S, 5.80. Found: C, 56.12; H, 6.47; S, 5.51.

Similarly, following the procedure of Example 7(b), 3-bromobenzaldehyde was reacted with 1-phenyl-1,7-diyne to yield 3-(8-phenyl-1,7-octadiynyl)benzaldehyde which was reduced to 3-(8-phenyloctyl)benzaldehyde and the latter was reacted as described in Example 35(a), (b) and (c) to give 3-(2-carboxyethylthio)-3-[3-(8-phenyloctyl)phenyl]-2-hydroxypropanoic acid, dipotassium salt, hydrate as a mixture of isomers, $-\log K_B$ value 6.2.

Analysis for $C_{26}H_{32}O_5S \cdot K_2 \cdot 2\frac{1}{4}H_2O$: Calculated: C, 54.28; H, 6.39. Found: C, 54.05; H, 6.14.

EXAMPLE 36

Resolution of 3-(2-Carboxyethylthio)-3-[2-(8-phenyloctyl)phenyl]-2-hydroxypropanoic acid

PROCEDURE I

The racemic dimethyl ester of Example 35(b) (28.0 g, 0.0576 moles) in 500 ml of pyridine under argon was treated with a suspension of the acid chloride of N-trichloroethoxycarbonyl-L-proline (89.0 g, 0.288 moles) in 500 ml of pyridine over 10 minutes at −5° C. The resulting yellow solution was warmed to 25° C. and stirred for 12 hours. The reaction mixture was concentrated and chromatographed on 1.5 Kg of silica gel using 25:75—ethyl acetate:hexane to give 43.7 g of a 1:1 mixture of prolyl disastereomers. Chromatography on 1.5 Kg of silica gel using 1:99—ethyl acetate: 1,2-dichloroethane gave 19.2 g (88%) of the desired 2S,3R diastereomer; $[\alpha]_D^{24°}$ C. = −58.6° (C=4, CHCl$_3$).

To a stirred solution of the 2S,3R prolyl ester (19.0 g, 0.025 moles) in 600 ml of 1,2-dimethoxyethane was added 200 ml of aqueous 0.75N lithium hydroxide over 10 minutes at 0° C. After stirring for 4 hours at 0° C., the reaction mixture was acidified to pH 6 with glacial acetic acid and concentrated to remove the 1,2-dimethoxyethane. The aqueous solution was cooled to 5° C., acidified to pH 3 with 3N hydrochloric acid, and extracted with ethyl acetate. The dried ethyl acetate solution was concentrated and chromatographed on 650 g of silica gel using 50:50:1—ethyl acetate:hexane:formic acid, followed by chromatography on 350 g of octadecylsilyl silica gel using 80:20:1—methanol:water:acetic acid to give 8.0 g (70%) of the desired 2(S)-hydroxy-3(R)-(2-carboxyethylthio)-3-[2-(8-phenyloctyl)phenyl]propanoic acid, $-\log K_B$ value 8.5; $[\alpha]_D^{24°}$ C. = −41.1° (C=1, CHCl$_3$).

PROCEDURE II

The racemic diacid of Example 35(c) (63.5 g, 0.138 moles) in 700 ml of isopropanol was treated with a solution of (R)-4-bromo-α-phenethylamine (57.1 g, 0.286 moles) in 200 ml of isopropanol at 25° C. The resulting solution was stirred for 3 hours, causing crystallization of the 2S,3R diamine salt. The suspension was cooled to 5° C., filtered, and the salt recrystallized twice from ethanol to give 37.7 g (72%) of 2S,3R diamine salt; m.p. 146°-147° C.; $[\alpha]_D^{24°}$ C.=−15.8° (C=1, CH$_3$OH).

The diamine salt (37.7 g, 0.0497 moles) was added in portions to 400 ml of cold 0.5N aqueous hydrochloric acid. The mixture was extracted with ethyl acetate, and the ethyl acetate solution washed three times with 0.5N hydrochloric acid. The ethyl acetate solution was washed with saturated sodium chloride solution, dried, and concentrated to give 19.5 g (97%) of the desired 2(S)-hydroxy-3(R)-(2-carboxyethylthio)-3-[2-(8-phenyloctyl)-phenyl]propanoic acid; $[\alpha]_D^{24°}$ C.=−40.8° (C=1, CHCl$_3$).

EXAMPLE 37

2(S)-Hydroxy-3(R)-(2-carboxyethylthio)-3-[2-(8-phenyloctyl)phenyl]propanoic acid, diarginine salt A solution of 2(S)-hydroxy-3(R)-(2-carboxyethylthio)-3-[2-(8-phenyloctyl)phenyl]propanoic acid (0.58 g, 1.27 mmoles) in 200 ml of methanol was treated with anhydrous arginine (0.441 g, 2.53 mmoles). The mixture was heated until solution was complete, and the solvent evaporated. The residue was triturated with acetone. Filtration and drying in vacuo gave the diarginine salt, 0.98 g (96%) as a free flowing white solid, mp 172°-176° C.

EXAMPLE 38

2(S)-Hydroxy-3(R)-(2-carboxyethylthio)-3-[2-(8-phenyloctyl)phenyl]propanoic acid, disodium salt A solution of 2(S)-hydroxy-3(R)-(2-carboxyethylthio)-3-[2-(8-phenyloctyl)phenyl]propanoic acid (3.18 g, 6.94 mmoles) in a mixture of 40 ml of ethanol and 0.4 ml of water was passed through a millipore (0.45 m) filter. The filtrate was treated with a solution of sodium hydroxide (0.556 g, 13.9 mmoles) in 27 ml of ethanol. The precipitated solid was filtered, washed with ethanol, and dried, in vacuo at 23° C. for 4 hours and 60° C. for 3 hours, to yield the disodium salt as a free flowing white powder, 3.12 g (89.7%), mp>220° C.

Analysis for C$_{26}$H$_{32}$O$_5$S.2Na.1/10 C$_2$H$_5$OH: Calculated: C, 61.54; H, 6.48; S, 6.32. Found: C, 61.47; H, 6.50; S, 6.33.

EXAMPLE 39

Preparation of 2-Hydroxy-3-(2-carboxyethylthio)-3-(2-undecyloxyphenyl)propanoic acid (a) 2-Undecyloxy-5-methoxybenzaldehyde To a solution of 2-hydroxy-5-methoxybenzaldehyde (10 g, 65.7 mmoles) in 100 ml of sieve-dried dimethylformamide was added freshly-pulverized potassium carbonate (10 g, 72.3 mmoles) and undecyl bromide (15 ml, 67.3 mmoles). The reaction mixture was stirred at 100° C. for 1 hour, cooled to room temperature and then poured into ice-cold water/hexane. The layers were separated and the organic extract was washed with ice-cold 5% sodium hydroxide solution, water and saturated sodium chloride solution. The organic layer was dried with anhydrous magnesium sulfate, treated with charcoal and concentrated in vacuo. The resulting yellow solid was recrystallized from hexane, to give 16.2 g (80%) of the product as a white solid.

(b) 2-Undecyloxy-5-hydroxybenzaldehyde

The 2-undecyloxy-5-methoxybenzaldehyde (16.2 g, 52.9 mmoles) in 100 ml of methanesulfonic acid was treated with L-methionine (16 g, 0.1057 mole) at room temperature for 48 hours. The reaction mixture was diluted with ethyl acetate and washed with ice-cold water and saturated sodium chloride solution. The organic extract was dried with anhydrous magnesium sulfate, treated with charcoal and the solvent was removed in vacuo. The resulting solid was recrystallized twice from hexane to give 7.7 g (50%) of the product as a white solid, mp 66°-67° C.

Analysis for C$_{18}$H$_{28}$O$_3$: Calculated: C, 73.93; H, 9.65. Found: C, 73.64; H, 9.56.

(c) 2-Hydroxy-3-(2-carboxyethylthio)-3-[2-(undecyloxy-5-hydroxyphenyl]propanoic acid Following the procedures of Example 35(a)–(c) and employing 2-undecycloxy-5-hydroxybenzaldehyde as the reactant, there was obtained the product.

Analysis for C$_{23}$H$_{36}$O$_7$S: Calculated: C, 60.50; H, 7.95. Found: C, 60.85; H, 8.12.

Similarly, employing 2-undecyloxybenzaldehyde from Example 19(a) and following the procedure of Example 35(a)–(c), there was obtained 2-hydroxy-3(2-carboxyethylthio)-3-(2-undecyloxyphenyl)propanoic acid, as the dipotassium salt, −log K$_B$ value 7.2.

Analysis for C$_{23}$H$_{34}$O$_6$S.K$_2$: Calculated: C, 53.46; H, 6.63; S, 6.20. Found: C, 53.22; H, 6.74; S, 6.02.

EXAMPLE 40

Preparation of 2-Hydroxy-3-(2-carboxyethylthio)-3-[2-(10-undecynloxy)phenyl]propanoic acid To an ice-cold solution of 11-hydroxyundecyne (10 g, 59.4 mmoles) in 400 ml of methylene chloride under argon was added in one portion carbon tetrabromide (40.5 g, 0.1224 mole). The reaction mixture was stirred at 0° C. for 5 minutes and triphenylphosphine (29.43 g, 0.1122 mole) was added. The reaction was kept at 0° C. for an additional 15 minutes and stirred at room temperature for 3 hours. The methylene chloride was removed in vacuo. The residue was treated with hexane and the combined organic extract was concentrated in vacuo. The crude product was purified by flash chromatography on silica, eluting with straight hexane, to give 7.2 g (52%) of 11-bromoundecyne as a colorless oil. Following the procedures of Examples 20 and 39(a), a mixture of salicylaldehyde, 11-bromoundecyne and potassium carbonate in dimethylformamide is reacted to furnish 2-(10-undecynyloxy)benzaldehyde.

By following the procedures of Example 35(a)–(c), from 2-(10-undecynyloxy)benzaldehyde there was obtained the product, as the dipotassium salt, −log K$_B$ value 6.7.

Analysis for C$_{23}$H$_{30}$O$_6$S.K$_2$: Calculated: C, 53.88; H, 5.90; S, 6.25. Found: C, 54.23; H, 5.94; S, 5.92.

EXAMPLE 41

Preparation of 3-(2-Carboxyethylthio)-3-(2-dodecylphenyl)-2-methoxypropanoic acid (a) Methyl 2-methoxy-3-hydroxy-3-(2-dodecylphenyl)propionate To a solution of di-i-propylamine (0.77 ml, 5 mmoles) in tetrahydrofuran (10 ml) at −78° C. was added n-butyl lithium (2.1 ml, 5.5 mmoles) under argon atmosphere. After 15 minutes, methyl methoxyacetate (0.52 g, 5 mmoles) in tetrahydrofuran (2 ml) was added dropwise, with stirring. The resulting enolate solution was stirrred at −78° C. for 45 minutes. A solution of 2-dodecylbenzaldehyde (1.65 g, 6 mmoles) in tetrahydrofuran (2 ml) was added. The resulting light-blue mixture became a suspension after 1.5 hours. The reaction mixture was quenched with saturated ammonium chloride solution, diluted with ether and ice-water. The aqueous phase was extracted with ether. The combined organic extract was washed with saturated sodium chloride solution, dried over magnesium sulfate, and evaporated to give the product, which was purified by flash column chromatography (silica, 15% ethyl acetate/hexane). The fractions were pooled to give 620 mg (33%).

(b) 3-(2-Carboxyethylthio)-3-(2-dodecylphenyl)-2-methoxypropionic acid

To a solution of trifluoroacetic acid (10 ml) and 3-mercaptopropionic acid (1 ml, 0.01 mole) at 0° C. under argon was added methyl 2-methoxy-3-hydroxy-3-(2-dodecylphenyl) propionate (0.45 g, 1.2 mmoles) all at once. The reaction mixture was stirred at room temperatures for 18 hours and evaporated. The residue was taken up in 80 ml of carbon tetrachloride and washed extensively with water. The organic phase was dried over magnesium sulfate and evaporated to give monomethyl ester, which was hydrolyzed in 2 ml of sodium hydroxide solution (10%) and 15 ml of methanol at room temperature for 18 hours. The reaction mixture was concentrated at reduced pressure and the residue was diluted with cold water, neutralized with hydrochloric acid solution (3N) to pH 3. The acidic aqueous phase was extracted with ether, the combined extract was dried over magnesium sulfate and then evaporated to give crude product. The product was purified by flash column chromatography (silica, 20% ethyl acetate in hexane with 0.3% formic acid). Fractions were pooled to give 165 mg (30%) of the mixutre of isomers, −log $K_B$ value 7.5.

Analysis for $C_{25}H_{40}O_5S$: Calculated: C, 66.34; H, 8.91; S, 7.08. Found: C, 66.40; H, 8.90; S, 6.72.

EXAMPLE 42

Preparation of 2-Methoxy-3-(2-carboxyethylthio)-3-[2-(8-phenyloctyl)phenyl]propanoic acid (a) Methyl 2-methoxy-3-hydroxy-3-[2-(8-phenyloctyl)phenyl]-propanoate To tetrahydrofuran (50 ml), cooled to −78° C. under argon, was added diisopropylamine (5.7 ml, 0.041 mole) followed by n-butyllithium (16 ml, 0.041 mole) slowly. After 15 minutes, methyl methoxyacetate (4.25 g, 0.041 mole) in tetrahydrofuran (10 ml) was added dropwise. The resulting solution was stirred for 30 minutes after which a solution of 2-(8-phenyloctyl)benzaldehyde in tetrahydrofuran (10 ml) was added dropwise. After 2 hours the reaction mixture was quenched with a solution of saturated ammonium chloride and then diluted with ice water. The aqueous layer was extracted with ether. The combined ether extract was washed with 10% sodium hydroxide (ice cold), dried over magnesium sulfate, filtered and evaporated to give the desired product.

(b) Methyl 2-methoxy-3-(2-carbomethoxyethylthio)-3-[2-(8-phenyloctyl)phenyl]propanoate.

To trifluoroacetic acid (100 ml) under argon and cooled to 0° C., was added methyl 3-mercaptopropanoate (0.5 ml, 4.5 mmoles). The mixture was stirred for 10 minutes, after which the ice bath was removed. Methyl 2-methoxy-3-hydroxy-3-[2-(8-phenyloctyl)phenyl]-propanoate (1.5 g, 4 mmoles) was added and the mixture stirred for 18 hours. The reaction mixture was evaporated and diluted in methylene chloride. The organic layer was washed with 10% sodium hydroxide (ice cold) followed by ice water. The organic layer was dried over magnesium sulfate, filtered and evaporated. Flash chromatography on silica gel provided the desired product.

(c) 2-Methoxy-3-(2-carboxyethylthio)-3-[2-(8-phenyloctyl)phenyl]propanoic acid

A solution of methyl 2-methoxy-3-(2-carbomethoxyethylthio)-3-[2-(8-phenyloctyl)phenyl]propanoate (0.5807 g, 1.2 mmoles) in methanol (5 ml) under argon was cooled to 0° C., after which 10% sodium hydroxide (1.5 ml, 3.5 mmoles) was added. The mixture was permitted to warm to room temperature and stirred for 2 hours. The methanol was evaporated and the mixture diluted with water. The pH of the aqueous layer was adjusted to 2 with dilute hydrochloric acid and extracted with ether. The organic phase was dried over magnesium sulfate, filtered and evaporated. The diastereomeric mixture of products was separated on a silica column using 23% ethyl acetate in hexane plus 0.5% formic acid. Five runs were made and the fractions analyzed on an analytical column. The separation provided both diastereomers in greater than 99% purity. The erythro isomer was obtained in 28% yield and the threo isomer in 22%.

Erythro isomer: Analysis for $C_{27}H_{36}SO_5 \cdot \frac{1}{2}H_2O$: Calculated: C, 68.28; H, 7.64. Found: C, 68.12; H, 7.63. Threo isomer: Analysis for $C_{27}H_{38}SO_5 \cdot \frac{1}{2}H_2O$: Calculated: C, 67.33; H, 7.53. Found: C, 67.18; H, 7.54.

EXAMPLE 43

Preparation of 2-Fluoro-3-(2-carboxyethylthio)-3-[2-(8-phenyloctyl)-phenyl]propanoic acid (a) Ethyl 2-fluoro-3-hydroxy-3-[2-(8-phenyloctyl)phenyl]-propanoate To a suspension of zinc dust (4.8 g, 0.074 mole) and copper (I) bromide in distilled tetrahydrofuran (250 ml) was added a solution of diethyl aluminum chloride (0.054 mole, 54 ml) in hexane while stirring under argon at 25° C. The resulting mixture was cooled to −20° C. and a solution of 2-(8-phenyloctyl) benaldehyde (0.049 mole, 14.5 g) and ethyl bromofluoroacetate (0.049 mole, 9.0 g) was added slowly over 90 minutes at −20° C. The reaction mixture was permitted to warm to room temperature. After 2 hours the zinc was filtered off and washed with ether. The solvents were evaporated and the residue flask chromatographed on silica gel eluted with 10% ethyl acetate in hexane to provide the desired product.

(b) Ethyl 2-(8-phenyloctyl-α-fluorocinnamate

The compound of Example 43(a) (0.03 mole, 12 g) was dissolved in methylene chloride (150 ml) and cooled to 0° C. Triethylamine (0.75 mole, 105 ml) was added, under argon, maintaining the temperature of 0° C. The mixture was cooled to −20° C. and methanesulfonyl chloride (0.45 mole, 35 ml) was added slowly. After the addition was complete, the reaction mixture was permitted to warm to room temperature. After 17 hours the mixture was washed with ice cold 3N hydrochloric acid, followed by ice water and sodium bicarbonate. The aqueous phase was washed with methylene chloride. The organic phase was dried over magnesium sulfate and activated charcoal, filtered and the methylene chloride evaporated, resulting in 10 g of crude product.

(c) 2-Fluoro-3-(2-carboxyethylthio)-3-[2-(8-phenyloctyl)phenyl]propanoic acid Sodium (0.52 mole, 12 g) was added in small amounts to methanol (400 ml), cooled to 0° C. under argon, and allowed to dissolve. After 1 hour all the sodium was in solution and 3-mercaptopropionic acid was added. The reaction mixture was permitted to warm to room temperature and the compound of Example 43(b) was added. After approximately 18 hours, the mixture was cooled to 0° C., water was added and then warmed to room temperature. Following hydrolysis, the mixture was cooled, acidified to pH 3 and extracted with ether. The organic layer was dried over magnesium sulfate, filtered and evaporated. The diastereomeric mixture was separated using a silica column, 25% ethyl acetate in hexane plus 0.5% formic acid, to yield 150 mg of erythro isomer and 40 mg of threo isomer; −log $K_B$ values for erythro isomer 7.4 and threo isomer 7.1. Erythro isomer analysis for $C_{26}H_{33}SO_4F$: Calculated: C, 67.14; H, 7.15. Found: C, 66.81; H, 7.31.

EXAMPLE 44

Preparation of 3-(2-Carboxyethylthio)-3-[2-(7-(3-trifluoromethylphenylthio)heptyl)phenyl]propanoic acid

(a) 2-(7-Bromoheptyl)benzoic acid

To a solution of freshly distilled tetrahydrofuran (200 ml), hexamethylphosphoramide (20 ml) and toluic acid (0.22 mole, 30 g), under argon and cooled to 0° C., was added n-butyllithium (0.44 mole, 170 ml). This mixture was added slowly to a solution of 1,6-dibromohexane (0.55 mole, 84 ml) in tetrahydrofuran (200 ml) and hexamethylphosphoramide (20 ml), cooled to 0° C. The reaction mixture was stirred at 0° for several hours. The tetrahydrofuran is evaporated and the reaction mixture was partitioned between ether and 1N sodium hydroxide (cold). The aqueous layer is removed and slowly acidified with concentrated hydrochloric acid to pH 8.5 The aqueous layer is extracted with ether.

The organic extract was dried over magnesium sulfate and filtered to yield 23 g of crude product. Flash chromatography using 7% ethyl acetate in hexane on silica gave the desired product.

(b) 2-(7-Bromoheptyl)benzyl alcohol

To 2-(7-bromoheptyl) benzoic acid (8.0 g, 0.027 mole) and distilled tetrahydrofuran (75 ml) was added diborane (40 ml, 0.04 mole) at room temperature under argon. The reaction mixture was stirred at room temperature for approximately 18 hours under argon, cooled to 0° C. and quenched with ethanol. The solvents were evaporated to give a colorless oil which was partitioned between methylene chloride and water. The organic layer was dried over magnesium sulfate and filtered. The resulting oil was flash chromatograhed on silica using 10% ethyl acetate in hexane to give the desired product.

(c) 2-(7-Bromoheptyl)benzaldehyde

To ethyl acetate (150 ml), cooled to 0° C., was added manganese oxide (15 g) followed by 2-(7-bromoheptyl) benzyl alcohol (3.39 g, 1.2 mmoles). The reaction mixture was permitted to warm to room temperature slowly, and stirred for 1 hour. The mixture was then cooled to 0° C. and stirred for 18 hours. Subsequently the mixture was filtered and evaporated to yield the desired product.

(d) 2-[7-(3-trifluoromethylphenylthio)heptyl]benzaldehyde

To N,N-dimethylformamide (30 ml) and 2-(7-bromoheptyl) benzaldehyde (1.5 g, 5 mmoles) was added a solution of 3-trifluoromethylthiophenol (1.0 ml, 8 mmoles) and triethylamine (3.0 ml, 0.02 mole) in N,N-dimethylformamide (20 ml). The reaction mixture was heated to 90° C. for 1 hour and then stirred for 1½ hours while slowly cooling to room temperature. The mixture was diluted with toluene and evaporated, followed by dilution with methylene chloride. The solution was evaporated and flash chromatographed using 8% ethyl acetate in hexane to give the desired product.

(e) t-Butyl 3-hydroxy-3-[2-(7-(3-trifluoromethylphenylthio)heptyl)phenyl]propanoate To a suspension of zinc dust (0.25 g, 3 mmoles) and cooper (I) bromide (0.02 g, 0.129 mmoles) in distilled tetrahydrofuran (20 ml) was added a solution of diethylaluminum chloride (2.8 ml, 2.8 mmoles) in hexane while stirring under argon at 25° C. The resulting mixture was cooled to −20° C., and a solution of 2-[7-trifluoromethylphenylthio)heptyl]benzaldehyde (1.08 g, 2.8 mmoles) and t-butyl bromoacetate (0.42 ml, 2.8 mmoles) in tetrahydrofuran (6 ml) was added slowly at −20° C. The reaction mixture was permitted to warm to room temperature. After 2 hours the zinc was filtered off and washed with ether. The solvents were evaporated and the residue flash chromatographed on silica gel, eluted with 10% ethyl acetate in hexane, to provide the desired product.

(f) 3-(2-Carboxyethylthio)-3-[2-(7-(3-trifluoromethylphenylthio)heptyl)phenyl]propanoic acid To trifluoroacetic acid (20 ml), cooled to 0° C., was added 3-mercaptopropionic acid (0.26 ml, 3 mmoles) followed by t-butyl 3-hydroxy-3-[2-(7-(3-trifluoromethylphenylthio)heptyl)phenyl]propanoate. The reaction mixture was stirred for 1 hour and evaporated. The resulting residue was diluted with carbon tetrachloride and washed with ice water. The organic layer was dried over sodium sulfate, filtered and evaporated. The resulting oil was flash chromatographed to give the desired product, −log $K_B$ value 6.8.

Analysis for $C_{26}H_{31}S_2O_4F_3$: Calculated: C, 59.07; H, 5.91. Found: C, 59.50; H, 6.02.

Similarly, following the procedures of Example 44(d)-(f), the indicated thiophenols were employed to give the corresponding products:

| Thiophenol | Product |
| --- | --- |
| 4-methoxythiophenol | 3-(2-carboxyethylthio)-3-[2-(7-(4-methoxyphenylthio)-heptyl)phenyl]propanoic acid, $-\log K_B$ value 5.6 |
| thiophenol | 3-(2-carboxyethylthio)-3-[2-(7-phenylthioheptyl)phenyl]propanoic acid, $-\log K_B$ value 5.9 |

EXAMPLE 45

Preparation of
2-Hydroxy-3-(2-carboxyethylthio)-3-[2-(8-(2-furyl)octyl)phenyl]propanoic acid (a) 2-(7-triphenylphosphonium bromoheptyl)benzoic acid A mixture of toluene (100 ml), triphenylphosphine (9.68 g, 37 mmoles) and 2-(7-bromoheptyl)benzoic acid (10 g, 0.033M), prepared as in Example 44(a) was heated to 80° C. for 3 days. The resulting gum was triturated with hexane, followed by methylene chloride, to give a tacky solid as the product.

(b) 2-[(7-(Z)-octenyl-8-(2-furyl)phenyl[benzoic acid

To tetrahydrofurn (75 ml), cooled to −60° C., was added 2-(7-triphenylphosphonium bromoheptyl) benzoic acid (4.3 g, 7.7 mmoles). To the resulting suspension was added n-butyllithium (6.55 ml, 0.02M) under argon slowly over a 20 minute period. The reaction mixture was then stirred for 40 minutes. Hexamethylphosphoramide (17.5 ml) was then added in one portion, followed by 2-furaldehyde (0.77 ml, 9 mmoles) in tetrahydrofuran (25 ml). The mixture was stirred for 20 minutes at −60° C., after which the reaction mixture was placed in an ice bath and allowed to slowly warm to room temperature. The solvent was evaporated and the residue partitioned between ether and cold 3N hydrochloric acid. The organic layer was dried over magnesium sulfate, filtered and evaporated. The resulting oil was flash chromatographed to give the desired product.

(c) [2-(8-(2-furyl)octyl)phenyl]]benzoic acid

In a hydrogenation flask was placed ethyl acetate (150 ml), 2-[(7-(Z)-octenyl-8-(2-furyl)phenyl]benzoic acid (1.8 g, 6 mmoles) and 10% palladium-on-charcoal (91 mg) over argon. The flask was hydrogenated for 4 hours. The mixture was then filtered and evaporated to give the desired product.

(d) [2-(8-(2-furyl)octyl)phenyl]benzyl alcohol

To freshly distilled tetrahydrofuran (30 ml), cooled to 0° C., was added in one portion lithium aluminum hydride (0.23 g, 5.8 mmoles). The mixture was stirred for 5 minutes, followed by addition of the compound of Example 45(c) while keeping the temperature at 0° C. The reaction mixture was quenched with ice water, followed by sodium hydroxide, and then water. The ether extract was dried over magnesium sulfate and filtered to obtained the desired product.

(e) [2-(8-(2-furyl)octyl)phenyl]benzaldehyde

A suspension of maganese oxide (10 g) and ethyl acetate (70 ml), under argon, was cooled to 0° C., to which was added the compound of Example 45(d) (1.4 g, 5 mmoles) in ethyl acetate (10 ml). The reaction mixture was permitted to warm up slowly to room temperature and stirred for 3 hours. The mixture was filtered and evaporated. The resulting oil was flash chromatographed on silica gel to provide the desired product.

(f) Methyl [2-(8-(2-furyl)octyl)phenyl]-2,3-epoxypropanoate

To methylene chloride (5 ml) and the compound of Example 45(e) (0.4561 g, 6 mmoles), under argon, was added methyl chloroacetate (0.2 ml, 22 mmoles) and the mixture cooled to −20° C. A 25% sodium methoxide in methanol solution (0.4 ml, 2 mmoles) was added quickly and the mixture was permitted to warm to 0° C. slowly. The mixture was stirred for one hour at 0° C. and then permitted to warm to room temperature. The mixture was quenched with ice and partitioned between cold water and methylene chloride. The organic phase was dried over magnesium sulfate, filtered and evaporated to provide the desired product.

(g) Methyl 2-hydroxy-3-(2-carbomethoxyethylthio)-3-[2-(8-(2-furyl)octyl)phenyl]propanoate To methanol (8.3 ml) containing 2% triethylamine was added the compound of Example 45(f) (0.4327 g, 1.2 mmoles) and the mixture stirred at room temperature under argon for 10 minutes. Methyl 3-mercaptopropionate (0.23 ml, 2 mmoles) and triethylamine (0.53 ml, 3 mmoles) were dissolved in methanol (5.3 ml) and added dropwise at room temperature to the above mixture. The reaction mixture was stirred at room temperature for 24 hours and then evaporated. The material was then chromatographed on aluminum using 20% ethyl acetate in hexane to obtain the desired product.

(h) 2-Hydroxy-3-(2-carboxyethylthio)-3-[2-(8-(2-furyl)octyl)phenyl]propanoic acid Methyl 2-hydroxy-3-(2-carbomethoxyethylthio)-3-[2-(8-(2-furyl)octyl)phenyl]propanoate (0.068 g, 0.14 mmoles) was dissolved in methanol (2.0 ml), under argon, cooled to 0° C. and a 1N sodium hydroxide solution (0.54 ml) was added dropwise. The ice bath was removed and the reaction mixture permitted to warm to room temperature. After 5 hours, the methanol was evaporated and the residue diluted with water. The pH of the aqueous layer was adjusted to 2 with dilute hydrochloric acid. The acidic layer was then extracted with ethyl acetate, dried over magnesium sulfate, filtered and evaporated. The residue was flash chromatographed on silica gel to provide the desired product as a mixture of diastereomers, $-\log K_B$ value 7.7.

Analysis for $C_{24}H_{32}SO_6$: Calculated: C, 62.38; H, 6.98. Found: C, 62.19; H, 7.15.

EXAMPLE 46

Preparation of
2-Hydroxy-3-(2-carboxyethylsulfinyl)-3-[2-(8-phenyloctyl)phenyl]propanoic acid A solution of the disodium salt of Example 38 (0.25 g, 0.5 mmole) in 5 ml of water at 0° C. was treated with a solution of sodium periodate (0.12 g, 0.56 mmole) in 3 ml of water. After stirring in the cold for 2 hours, the solution was acidified with hydrochloric acid and extracted with ether. The extract was washed with water, dried and evaporated, to give the product as an oil, 230 mg, as a mixture of diastereomeric sulfoxides.

EXAMPLE 47

Preparation of
2-Hydroxy-3-(2-carboxyethylsulfonyl)-3-[2-(8-phenyloctyl)phenyl]propanoic acid A solution of the compound of Example 36 (0.11 g, 0.24 mmole) in 3 ml of chloroform at 23° C. was treated with 85% m-chloroperbenzoic acid (0.107 g, 0.53 mmole) portionwise. The solution was stirred 3 hours, and excess peroxide was destroyed by the addition of 5 ml 10% aqueous sodium bisulfite. The mixture was stirred 10 minutes, acidified with hydrochloric acid, and the layers separated. The organic layer was washed with water, dried, and the solvent evaporated.

The residue was chromatographed over a silica gel column. Elution with ethyl acetate/hexane/acetic acid (50/49/1) removed m-chlorobenzoic acid. Further elution with ethyl acetate/methanol/acetic acid (90/5/5) gave the product as an oil, 80 mg.

EXAMPLE 48

As a specific embodiment of a composition of this invention, an active ingredient, such as the compound of Example 9(b), 35(c), 36, 37 or 38 is dissolved in 25 mM sodium carbonate at a concentration of 0.4 percent and aerosolized from a nebulizer operating at an air flow adjusted to deliver the desired aerosolized weight of drug.

EXAMPLE 49

As an additional specific embodiment of a composition of this invention, an active ingredient, such as the compound of Example 14(f), 35(c), 36, 37 or 38 is admixed with mannitol at a concentration of 1.0 percent and administered from a powder inhalation device adjusted to deliver the desired weight of drug.

We claim:

1. A compound represented by the following structural formula (I):

wherein
$R_1$ is $C_8$ to $C_{13}$ alkyl, $C_7$ to $C_{12}$ alkoxy, $C_7$ to $C_{12}$ alkylthio, $C_{10}$ to $C_{12}$ 1-alkynyl, 10-undecynyloxy, 11-dodecynyl, phenyl-$C_4$ to $C_{10}$ alkyl, phenyl-$C_3$ to $C_9$ alkoxy, phenylthio-$C_3$ to $C_9$ alkyl with the phenyl optionally mono substituted with bromo, chloro, trifluoromethyl, $C_1$ to $C_4$ alkoxy, methylthio or trifluoromethylthio, furyl-$C_4$ to $C_{10}$ alkyl, trifluoromethyl-$C_7$ to $C_{12}$ alkyl or cyclohexyl-$C_4$ to $C_{10}$ alkyl;

$R_2$ is hydrogen, bromo, chloro, methyl, trifluoromethyl, hydroxy, $C_1$ to $C_4$ alkoxy or nitro; or $R_1$ is hydrogen and $R_2$ is $C_8$ to $C_{13}$ alkyl, $C_7$ to $C_{12}$ alkoxy, $C_7$ to $C_{12}$ alkylthio, $C_{10}$ to $C_{12}$ 1-alkynyl, 10-undecynyloxy, 11-dodecynyl, phenyl-$C_4$ to $C_{10}$ alkyl, phenyl-$C_3$ to $C_9$ alkoxy, phenylthio-$C_3$ to $C_9$ alkyl with the phenyl optionally mono substituted with bromo, chloro, trifluoromethyl, $C_1$ to $C_4$ alkoxy, methylthio or trifluoromethylthio, furyl-$C_4$ to $C_{10}$ alkyl, trifluoromethyl$C_7$ to $C_{12}$ alkyl or cyclohexyl-$C_4$ to $C_{10}$ alkyl;

q is 0, 1 or 2, with the proviso that any of $R_1$ and $R_2$ above are not alkylthio or phenylthioalkyl when q is 1 or 2;

Y is, $$\begin{array}{c} CH(CH_2)_mCOR_3 \\ | \\ R_4 \end{array}$$

or $R_3$ is hydroxy or amino;
$R_4$ is $C_1$ to $C_4$ alkoxy, or hydroxy;
m is 0 or 1;
R is $$\begin{array}{c} (CH_2)_nCHCOR_6, \\ | \\ R_5 \end{array}$$

$CH(CO_2H)CH_2CO_2H$, $CH_2CH_2Z$ or n is 0 to 6;
$R_5$ is hydrogen, amino, or $NHCOCH_2CH_2CH(NH_2)CO_2H$;
$R_6$ is hydroxy, amino or $NHCH_2CO_2H$;
Z is $SO_3H$, $SO_2NH_2$ or $CN$;
$R_7$ is hydrogen, $C_1$ to $C_4$ alkyl or $C_3$ to $C_4$ alkenyl;
$R_8$ is hydrogen, $C_1$ to $C_4$ alkyl, carboxyl or carboxamido, or $(CH_2)_pCO_2H$, wherein p is 1 or 2, when $R_7$ and $R_9$ are hydrogen or $C_1$ to $C_4$ alkyl; and
$R_9$ is hydrogen, $C_1$ to $C_4$ alkyl or $CH_2CO_2H$, with the proviso that when n is 0, $R_5$ is hydrogen and further that $R_7$, $R_8$ and $R_9$ are not all hydrogen; or a pharmaceutically acceptable salt thereof.

2. A compound of claim 1 wherein R is $(CH_2)_{1-3}CO_2H$ or

3. A compound of claim 1 represented by the following structural formula (VI):

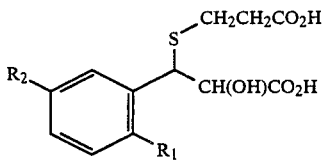

wherein R₂ is hydrogen.

4. A compound of claim 3 wherein R₁ is a phenyl—C₄ to C₁₀ alkyl radical.

5. A compound of claim 3 which is erythro-3-(2-carboxyethylthio)-3-(2-dodecylphenyl)-2-hydroxypropanoic acid.

6. A compound of claim 4 which is erythro-3-(2-carboxyethylthio)-3-[2-(8-phenyloctyl)phenyl]-2-hydroxypropanoic acid or a pharamceutically acceptable salt thereof.

7. A resolved diastereomer of claim 6 which is 2(S)-hydroxy-3(R)-(2-carboxyethylthio)-3-[2-(8-phenyloctyl)phenyl]propanoic acid, or a pharmaceutically acceptable salt thereof.

8. The compound of claim 7 in the form of its diarginine salt.

9. The compound of claim 7 in the form of its disodium salt.

10. The compound of claim 7 in the form of its dimagnesium salt.

11. A compound of claim 1 which is 5-(2-dodecylphenyl)-4-hydroxy-5-(1-methyl-5-carboxy-2-imidazolylthio)pentanoic acid.

12. A pharmaceutical composition for inhibiting the effects of leukotriene comprising a pharmaceutical carrier or diluent and a nontoxic amount sufficient to produce said inhibition of a compound of claim 1, formula (I).

13. A pharmaceutical composition according to claim 12 in a form suitable for administration by inhalation, parenteral administration, oral administration or topical administration.

14. A pharmaceutical composition according to claim 12 in which the compound is 2(S)-hydroxy-3-(R)-(2-carboxyethylthio)-3-[2-(8-phenyloctyl)phenyl]propanoic acid or a pharmaceutically acceptable salt thereof.

15. A pharmaceutical composition for inhibiting antigen-induced respiratory anaphylaxis comprising a pharmaceutical carrier or diluent and nontoxic amounts sufficient to produce said inhibition of a compound of claim 1, formula (I), and an histamine H₁-receptor antagonist.

16. A pharmaceutical composition according to claim 15 in which the active ingredients are 2(S)-hydroxy-3(R)-(2-carboxyethylthio)-3-[2-(8-phenyloctyl)phenyl]propanoic acid, or a pharmaceutically acceptable salt thereof, and 2-[4-(5-bromo-3-methylpyrid-2-yl)butylamino]-5-[(6-methylpyrid-3-yl)methyl]-4-pyrimidone.

17. A compound of claim 1 which is 3-(2-crboxyethylthio)-3-(2-undecyloxyphenyl)-2-hydroxypropanoic acid; erythro-3-(2-carboxyethylthio)-3-[2-(8-phenyloctyl)phenyl]-2-fluoropropanoic acid; or 3-(2-carboxyethylthio)-3-[2-(8-(2-furyl)octyl)phenyl]-2-hydroxypropanoic acid.

18. A compound of claim 1 which is 2-hydroxy-3-(2-carboxyethylsulfinyl)-3-[2-(8-phenyloctyl)phenyl]propanoic acid; or 2-hydroxy-3-(2-carboxyethylsulfonyl)-3-[2-(8-phenyloctyl)phenyl[propanoic acid.

19. A method of treating a pulmonary disease in which leukotrienes are a factor in a subject in need thereof comprising administration to such subject an effective amount of a compound of claim 1.

20. A method of treating a pulmonary disease in which leukotrienes are a factor in a subject in need thereof comprising administration to such subject an effective amount of a compound of claim 2.

21. A method of treating a non-pulmonary disease in which leukotrienes are a factor in a subject in need thereof comprising aministration to such subject an effective amount of a compound of claim 1.

22. A method of treating a non-pulmonary disease in which leukotrienes are a factor in a subject in need thereof comprising administration to such subject an effective amount of a compound of claim 7.

23. The compound of claim 7 in the form of its ethylenediamine salt.

24. The compound of claim 7 in the form of its piperazine salt.

25. The compound of claim 7 in the form of its zinc salt.

26. A pharmaceutical composition according to claim 12 in which the compound is erythro-3-(2-carboxyethylthio)-3-[2-(8-phenyloctyl)phenyl]-2-hydroxypropanoic acid or a pharmaceutically acceptable salt thereof.

27. A pharmaceutical composition according to claim 15 in which the active ingredients are 2(S)-hydroxy-3(R)-(2-carboxyethylthio)-3-[2-(8-phenyloctyl)phenyl]propanoic acid and an histamine H₁-receptor antagonist.

28. A pharmaceutical composition according to claim 15 in which the active ingredients are 2(S)-hydroxy-3(R)-(2-carboxyethylthio)-3-[2-(8-phenyloctyl)phenyl]propanoic acid, or a pharmaceutically acceptable salt thereof, and mepyramine.

29. A method of treating asthma in a subject in need thereof comprising administration to such subject of an effective amount of a compound of claim 1.

30. A method of treating allergic rhinitis in a subject in need thereof comprising administration to such subject of an effective amount of a compound of claim 1.

31. A method of treating uveitis or allergic conjunctivitis in a subject in need thereof comprising administration to such subject of an effective amount of a compound of claim 1.

32. A method of treating a pulmonary disease in which leukotrienes are a factor in a subject in need thereof comprising administration to such subject of an effective amount of a compound of claim 6.

33. A method of treating a non-pulmonary disease in which leukotrienes are a factor in a subject in need thereof comprising administration to such subject of an effective amount of a compound of claim 6.

34. A method of treating asthma in a subject in need thereof comprising administration to such subject of an effective amount of a compound of claim 6.

35. A method of treating asthma in a subject in need thereof comprising administration to such subject of an effective amount of a compound of claim 7.

36. A method of treating allergic rhinitis in a subject in need thereof comprising administration to such subject of an effective amount of a compound of claim 6.

37. A method of treating allergic rhinitis in a subject in need thereof comprising administration to such subject of an effective amount of a compound of claim 7.

38. A method of treating uveitis or allergic conjunctivitis in a subject in need thereof comprising administration to such subject of an effective amount of a compound of claim 7.

39. A method of treating uveitis or allergic conjunctivitis in a subject in need thereof comprising administration to such subject of an effective amount of a compound of claim 6.

* * * * *